United States Patent [19]
Caput et al.

[11] Patent Number: 6,022,856
[45] Date of Patent: Feb. 8, 2000

[54] TYPE-2 NEUROTENSIN RECEPTOR (NT-R2)

[75] Inventors: Daniel Caput, Avignolet Lauragais; Pascale Chalon, Fourquevaux; Pascual Ferrara, Avignolet Lauragais; Natalio Vita, Montgiscard, all of France

[73] Assignee: Sanofi, Paris, France

[21] Appl. No.: 08/858,876

[22] Filed: May 19, 1997

[30] Foreign Application Priority Data

Mar. 17, 1997 [FR] France ................................ 97 03204

[51] Int. Cl.⁷ ........................ A61K 38/17; C07K 14/705
[52] U.S. Cl. .............................. 514/12; 530/350
[58] Field of Search ................. 530/350; 514/2, 514/8, 12

[56] References Cited

FOREIGN PATENT DOCUMENTS 8143597  6/1996  Japan .

OTHER PUBLICATIONS

Chalon, et al.; "Molecular Cloning Of A Levocabastine–Sensitive Neurotensin Binding Site"; *FEBS Letters,* vol. 386 May 20, 1996; pp. 91–94.

Mazella, et al.; "Structure, Functional Expression, And Cerebral Localization Of The Levocabastine–Sensitive Neurotensin/Neuromedin N Receptor From Mouse Brain"; *The Journal of Neuroscience,* 16(18) Sep. 15, 1996; pp. 5613–5619.

Vita, et al.; "Cloning And Expression Of A Complementary DNA Encoding A High Affinity Human Neurotensin Receptor"; *FEBS Letters,* 317 (1,2), Feb. 8, 1993; pp. 139–142.

*Primary Examiner*—Marianne P. Allen
*Attorney, Agent, or Firm*—Jacobson, Price, Holman & Stern, PLLC

[57] ABSTRACT

This invention relates to a purified polypeptide which constitutes the type-2 neurotensin receptor (NT-R2), as well as the nucleotide sequence encoding this polypeptide.

2 Claims, 8 Drawing Sheets

```
         ┌── hNT-R1
         │── hNT-R2
         │
         │  1 .............................METSSPRPPRPSSNPGLSL.  19
         │                                 :...:  ...:.    .|:..|.
         └─ 1 MRLNSSAPGTPGTPAADPFQRAQAGLEEALLAPGFGNASGNASERVLAAP  50

20 DARLGVDTRLWAKVLFTALYALIWALGAAGNALSVHVVLKARA..GRAGR  67
            ..  |:|:|  ::.|||.||:|    ::..:|..||.:..  .. : :.   : .:
         51 SSELDVNTDIYSKVLVTAVYLALFVVGTVGNTVTAFTLARKKSLQSLQST 100

68 LRHHVLSLALAGLLLLLVGVPVELYSFVWFHYPWVFGDLGCRGYYFVHEL 117
            ::.|: ||||.:|  ||:::|||||.|:|.|.|| .||  |||||||:::
        101 VHYHLGSLALSDLLTLLLAMPVELYNFIWVHHPWAFGDAGCRGYYFLRDA 150

118 CAYATVLSVAGLSAERCLAVCQPLRARSLLTPRRTRWLVALSWAASLGLA 167
            |.|||.|.||:| .||:||:|:|::  :.|:...||:..:.  | || |.
        151 CTYATALNVASLSVERYLAICHPFKAKTLMSRSRTKKFISAIWLASALLT 200

168 LPMAVIMGQKHELETADGEPEPASRVCTVLVSRTALQVFIQVNVLVSFVL 217
            :||  ..||:.:    .|||:  .:::   ||.  :  ...:.|.||||.::||::
        201 VPMLFTMGEQN..RSADGQ.HAGGLVCTPTIHTATVKVVIQVNTFMSFIF 247

218 PLALTAFLNGVTVSHLLALCSQVPSTSTPGSSTPSRLELLSEEGLLSFIV 267
            |:.:...||.:....|   .:..|.:                |:|  ::
        248 PMVVISVLNTIIANKLTVMVRQAA................EQGQVC... 277

268 WKKTFIQGGQVSLVRHKDVRRIRSLQRSVQVLRAIVVMYVICWLPYHARR 317
            :.|::   .:  .   :.  |:..|.::|.|||||:|: :|:||||||.||
        278 ....TVGGEHSTFSMAIEPGRVQALRHGVRVLRAVVIAFVVCWLPYHVRR 323

318 LMYCYVPDDAWTDPLYNFYHYFMVTNTLFYVSSAVTPLLYNAVSSSFRK 367
            ||:||:.|:.||. ||:||||||||!.||||||.:.|||  ||..||.
        324 LMFCYISDEQWTPFLYDFYHYFMVTNALFYVSSTINPILYNLVSANFRH 373

368 LFLEAVSSLCGEHHPMKRLPPKPQSPTLMDTASGFGDPPETRT.. 410
            :||..:.:||.  :..::  |:  ....:.  :...  .::  :.   |
        374 IFLATLACLCPVWRRRKRPAFSRKADSVSSNHTLSSNATRETLY 418
```

FIG.2

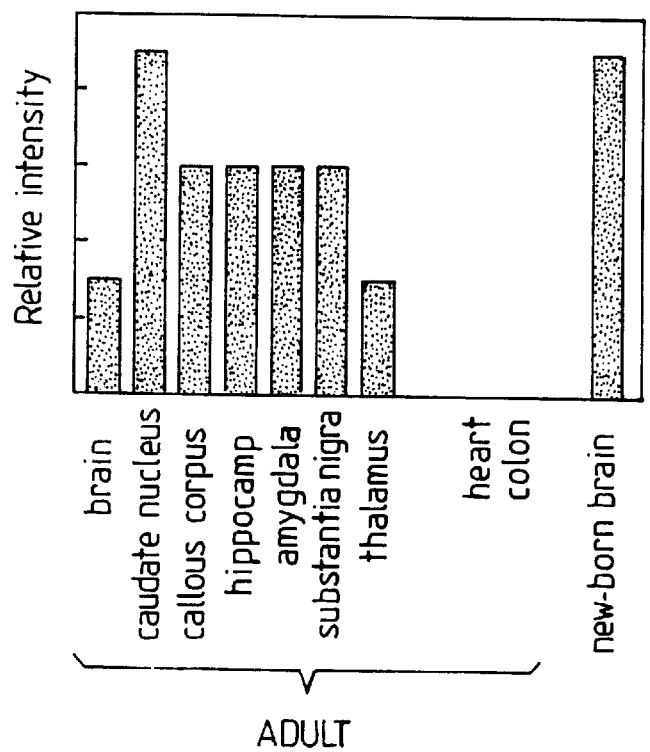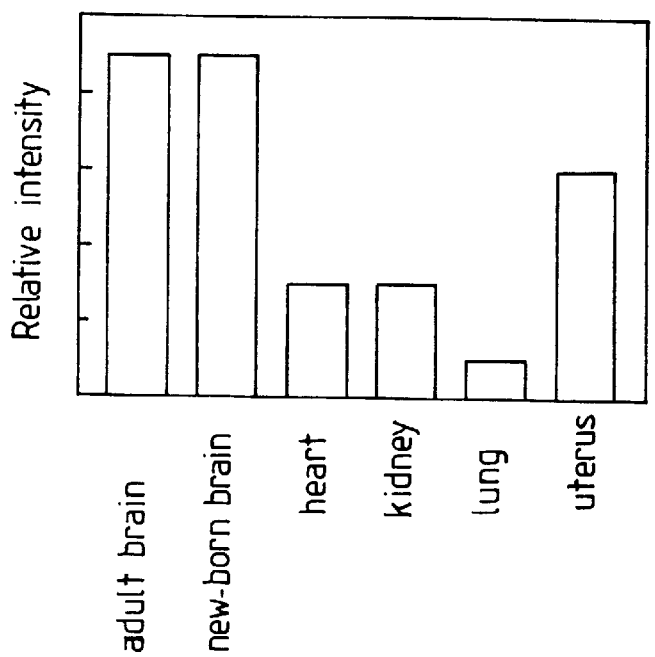
FIG.4b

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 1575 base pairs
      (B) TYPE: nucleic acid
      (C) STRANDEDNESS: single
      (D) TOPOLOGY: linear (ii) MOLECULE TYPE: cDNA (vi) ORIGINAL SOURCE:
      (A) ORGANISM: Homo sapiens (ix) FEATURE:
      (A) NAME/KEY: CDS
      (B) LOCATION: 37..1266

(xi) SEQUENCE DESCRIPTION: SEQ ID NO:1 :

```
GAGTGAGAGG GAGGGAGCGC CGGCCGCGGG AGCGGG ATG GAA ACC AGC AGC CCG         54
                                       Met Glu Thr Ser Ser Pro
                                        1               5

CGG CCC CCG CGG CCC AGC TCC AAC CCG GGG CTG AGC CTG GAC GCC CGG         102
Arg Pro Pro Arg Pro Ser Ser Asn Pro Gly Leu Ser Leu Asp Ala Arg
             10                  15                  20

CTG GGC GTG GAC ACT CGC CTC TGG GCC AAG GTG CTG TTC ACC GCG CTC         150
Leu Gly Val Asp Thr Arg Leu Trp Ala Lys Val Leu Phe Thr Ala Leu
         25                  30                  35

TAC GCA CTC ATC TGG GCG CTG GGC GCG GCG GGC AAT GCG CTG TCC GTG         198
Tyr Ala Leu Ile Trp Ala Leu Gly Ala Ala Gly Asn Ala Leu Ser Val
     40                  45                  50

CAC GTG GTG CTG AAG GCG CGG GCC GGG CGC GCG GGG CGC CTG CGC CAC         246
His Val Val Leu Lys Ala Arg Ala Gly Arg Ala Gly Arg Leu Arg His
 55                  60                  65                  70

CAC GTG CTC AGC CTG GCG CTC GCG GGC CTG CTG CTG CTG GTC GGC             294
His Val Leu Ser Leu Ala Leu Ala Gly Leu Leu Leu Leu Val Gly
                 75                  80                  85
```

-continued

| | |
|---|---|
| GTG CCG GTG GAG CTC TAC AGC TTC GTG TGG TTC CAC TAC CCC TGG GTC<br>Val Pro Val Glu Leu Tyr Ser Phe Val Trp Phe His Tyr Pro Trp Val<br>90 95 100 | 342 |
| TTC GGC GAC CTG GGC TGC CGC GGC TAC TAC TTC GTG CAC GAG CTG TGC<br>Phe Gly Asp Leu Gly Cys Arg Gly Tyr Tyr Phe Val His Glu Leu Cys<br>105 110 115 | 390 |
| GCC TAC GCC ACG GTG CTG AGC GTG GCA GGC CTG AGC GCC GAG CGC TGC<br>Ala Tyr Ala Thr Val Leu Ser Val Ala Gly Leu Ser Ala Glu Arg Cys<br>120 125 130 | 438 |
| CTA GCC GTG TGC CAG CCC CTG CGT GCC CGC AGC CTG CTG ACG CCA CGC<br>Leu Ala Val Cys Gln Pro Leu Arg Ala Arg Ser Leu Leu Thr Pro Arg<br>135 140 145 150 | 486 |
| CGG ACC CGG TGG CTG GTG GCG CTC TCG TGG GCC GCC TCG CTC GGC CTC<br>Arg Thr Arg Trp Leu Val Ala Leu Ser Trp Ala Ala Ser Leu Gly Leu<br>155 160 165 | 534 |
| GCC CTG CCC ATG GCC GTC ATC ATG GGG CAG AAG CAC GAA CTC GAG ACG<br>Ala Leu Pro Met Ala Val Ile Met Gly Gln Lys His Glu Leu Glu Thr<br>170 175 180 | 582 |
| GCG GAC GGG GAG CCG GAG CCC GCC TCG CGA GTG TGC ACG GTG CTG GTG<br>Ala Asp Gly Glu Pro Glu Pro Ala Ser Arg Val Cys Thr Val Leu Val<br>185 190 195 | 630 |
| AGC CGC ACC GCG CTC CAA GTC TTT ATC CAG GTG AAT GTG CTG GTG TCC<br>Ser Arg Thr Ala Leu Gln Val Phe Ile Gln Val Asn Val Leu Val Ser<br>200 205 210 | 678 |
| TTC GTG CTC CCC TTG GCA CTA ACT GCT TTC CTG AAT GGG GTC ACA GTG<br>Phe Val Leu Pro Leu Ala Leu Thr Ala Phe Leu Asn Gly Val Thr Val<br>215 220 225 230 | 726 |
| AGC CAC CTG CTG GCC CTC TGC TCC CAA GTG CCG TCC ACT TCT ACC CCG<br>Ser His Leu Leu Ala Leu Cys Ser Gln Val Pro Ser Thr Ser Thr Pro<br>235 240 245 | 774 |
| GGC AGC TCC ACC CCC AGC CGC CTG GAG CTG CTG AGT GAG GAG GGT CTC<br>Gly Ser Ser Thr Pro Ser Arg Leu Glu Leu Leu Ser Glu Glu Gly Leu<br>250 255 260 | 822 |
| CTC AGC TTC ATC GTA TGG AAG AAG ACC TTT ATC CAG GGA GGC CAG GTC<br>Leu Ser Phe Ile Val Trp Lys Lys Thr Phe Ile Gln Gly Gly Gln Val<br>265 270 275 | 870 |
| AGC CTG GTG AGA CAT AAA GAC GTG CGC CGG ATC CGC AGC CTC CAG CGC<br>Ser Leu Val Arg His Lys Asp Val Arg Arg Ile Arg Ser Leu Gln Arg<br>280 285 290 | 918 |
| AGC GTC CAG GTT CTC AGA GCC ATC GTG GTC ATG TAT GTC ATC TGC TGG<br>Ser Val Gln Val Leu Arg Ala Ile Val Val Met Tyr Val Ile Cys Trp<br>295 300 305 310 | 966 |
| CTG CCG TAC CAT GCC CGC AGG CTC ATG TAC TGC TAC GTA CCT GAT GAC<br>Leu Pro Tyr His Ala Arg Arg Leu Met Tyr Cys Tyr Val Pro Asp Asp<br>315 320 325 | 1014 |
| GCG TGG ACT GAC CCA CTG TAC AAT TTC TAC CAC TAC TTC TAC ATG GTG<br>Ala Trp Thr Asp Pro Leu Tyr Asn Phe Tyr His Tyr Phe Tyr Met Val<br>330 335 340 | 1062 |
| ACC AAC ACA CTT TTC TAC GTC AGC TCA GCT GTG ACT CCT CTT CTC TAC<br>Thr Asn Thr Leu Phe Tyr Val Ser Ser Ala Val Thr Pro Leu Leu Tyr<br>345 350 355 | 1110 |
| AAC GCC GTG TCC TCC TCC TTC AGA AAA CTC TTC CTG GAA GCC GTC AGC<br>Asn Ala Val Ser Ser Ser Phe Arg Lys Leu Phe Leu Glu Ala Val Ser<br>360 365 370 | 1158 |
| TCC CTG TGT GGA GAG CAC CAC CCC ATG AAG CGG TTA CCC CCG AAG CCC<br>Ser Leu Cys Gly Glu His His Pro Met Lys Arg Leu Pro Pro Lys Pro<br>375 380 385 390 | 1206 |
| CAG AGT CCC ACC CTA ATG GAT ACA GCT TCA GGC TTT GGG GAT CCC CCA<br>Gln Ser Pro Thr Leu Met Asp Thr Ala Ser Gly Phe Gly Asp Pro Pro | 1254 |

```
                395                 400                 405
GAA ACC CGG ACC TGAATGTAAT GCAAGAATGA ACAGAACAAG CAAAATGACC      1306
Glu Thr Arg Thr
            410

AGCTGCTTAG TCACCTGGCA AAGCAGGTGA GCAACCTCAT CACTAATCAT TCAAGCTT  1366

CAGCCAGGGC GACTTCTATC AACCCCTGCT CTGCTGAGAA CCATCAAGCG CAGGGAAG  1426

ACGTGACCCC TCCTAGCCTC AGGCTCCCTC GTCTGTGTAG TGGAGATAAA GAACAGCA  1486

CATCTCTTAG TGTTGCCTGA GACTAAAGTG CTTAGCACAG AACCTGGTGC GTAGTAGA  1546

CTCAATAAAT TTTTGCTGGC ACGAAAAAA                                  1575

(2) INFORMATION FOR SEQ ID NO: 2:

(i) SEQUENCE CHARACTERISTICS:
        (A) LENGTH: 410 amino acids
        (B) TYPE: amino acid
        (D) TOPOLOGY: linear (ii) MOLECULE TYPE: protein (xi) SEQUENCE DESCRIPTION: SEQ ID NO: 2:

Met Glu Thr Ser Ser Pro Arg Pro Pro Arg Pro Ser Ser Asn Pro Gly
1               5                   10                  15

Leu Ser Leu Asp Ala Arg Leu Gly Val Asp Thr Arg Leu Trp Ala Lys
                20                  25                  30

Val Leu Phe Thr Ala Leu Tyr Ala Leu Ile Trp Ala Leu Gly Ala Ala
            35                  40                  45

Gly Asn Ala Leu Ser Val His Val Val Leu Lys Ala Arg Ala Gly Arg
        50                  55                  60

Ala Gly Arg Leu Arg His His Val Leu Ser Leu Ala Leu Ala Gly Leu
65                  70                  75                  80

Leu Leu Leu Leu Val Gly Val Pro Val Glu Leu Tyr Ser Phe Val Trp
                85                  90                  95

Phe His Tyr Pro Trp Val Phe Gly Asp Leu Gly Cys Arg Gly Tyr Tyr
                100                 105                 110

Phe Val His Glu Leu Cys Ala Tyr Ala Thr Val Leu Ser Val Ala Gly
            115                 120                 125

Leu Ser Ala Glu Arg Cys Leu Ala Val Cys Gln Pro Leu Arg Ala Arg
        130                 135                 140

Ser Leu Leu Thr Pro Arg Arg Thr Arg Trp Leu Val Ala Leu Ser Trp
145                 150                 155                 160

Ala Ala Ser Leu Gly Leu Ala Leu Pro Met Ala Val Ile Met Gly Gln
                165                 170                 175

Lys His Glu Leu Glu Thr Ala Asp Gly Glu Pro Glu Pro Ala Ser Arg
            180                 185                 190

Val Cys Thr Val Leu Val Ser Arg Thr Ala Leu Gln Val Phe Ile Gln
        195                 200                 205

Val Asn Val Leu Val Ser Phe Val Leu Pro Leu Ala Leu Thr Ala Phe
        210                 215                 220

Leu Asn Gly Val Thr Val Ser His Leu Leu Ala Leu Cys Ser Gln Val
225                 230                 235                 240

Pro Ser Thr Ser Thr Pro Gly Ser Ser Thr Pro Ser Arg Leu Glu Leu
                245                 250                 255

Leu Ser Glu Glu Gly Leu Leu Ser Phe Ile Val Trp Lys Lys Thr Phe
            260                 265                 270
```

```
Ile Gln Gly Gly Gln Val Ser Leu Val Arg His Lys Asp Val Arg Arg
            275                 280                 285

Ile Arg Ser Leu Gln Arg Ser Val Gln Val Leu Arg Ala Ile Val Val
290                 295                 300

Met Tyr Val Ile Cys Trp Leu Pro Tyr His Ala Arg Arg Leu Met Tyr
305                 310                 315                 320

Cys Tyr Val Pro Asp Asp Ala Trp Thr Asp Pro Leu Tyr Asn Phe Tyr
                325                 330                 335

His Tyr Phe Tyr Met Val Thr Asn Thr Leu Phe Tyr Val Ser Ser Ala
            340                 345                 350

Val Thr Pro Leu Leu Tyr Asn Ala Val Ser Ser Ser Phe Arg Lys Leu
        355                 360                 365

Phe Leu Glu Ala Val Ser Ser Leu Cys Gly Glu His His Pro Met Lys
    370                 375                 380

Arg Leu Pro Pro Lys Pro Gln Ser Pro Thr Leu Met Asp Thr Ala Ser
385                 390                 395                 400

Gly Phe Gly Asp Pro Pro Glu Thr Arg Thr
                405                 410
```

(2) INFORMATION FOR SEQ ID NO: 3:

(i) SEQUENCE CHARACTERISTICS:
        (A) LENGTH: 1529 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Rat (ix) FEATURE:
        (A) NAME/KEY: CDS
        (B) LOCATION: 41..1288

(xi) SEQUENCE DESCRIPTION: SEQ ID NO: 3:

```
TGAGTGAGAG GGAGGGAGCT CAGGCCACCA CGAGACAGAG ATG GAG ACC AGC AGT        55
                                            Met Glu Thr Ser Ser
                                            1               5

CCG TGG CCT CCG AGG CCC AGC CCC AGC GCA GGG CTG AGC CTG GAG GCG       103
Pro Trp Pro Pro Arg Pro Ser Pro Ser Ala Gly Leu Ser Leu Glu Ala
            10                  15                  20

CGG CTG GGC GTG GAC ACT CGC CTC TGG GCC AAG GTG CTG TTC ACC GCG       151
Arg Leu Gly Val Asp Thr Arg Leu Trp Ala Lys Val Leu Phe Thr Ala
        25                  30                  35

CTC TAC TCG CTC ATC TTC GCA TTT GGC ACA GCG GGC AAT GCG CTG TCC       199
Leu Tyr Ser Leu Ile Phe Ala Phe Gly Thr Ala Gly Asn Ala Leu Ser
    40                  45                  50

GTG CAC GTG GTG CTG AAG GCG CGG GCC GGT CGC CCC GGG CGC CTG CGC       247
Val His Val Val Leu Lys Ala Arg Ala Gly Arg Pro Gly Arg Leu Arg
55                  60                  65

TAC CAC GTG CTC AGC CTG GCG CTC TCA GCC CTG CTG CTA CTG CTG GTC       295
Tyr His Val Leu Ser Leu Ala Leu Ser Ala Leu Leu Leu Leu Leu Val
70                  75                  80                  85

AGC ATG CCC ATG GAG CTC TAC AAC TTC GTG TGG TCC CAC TAC CCA TGG       343
Ser Met Pro Met Glu Leu Tyr Asn Phe Val Trp Ser His Tyr Pro Trp
            90                  95                  100

GTC TTC GGC GAT CTG GGC TGC CGT GGC TAT TAC TTC GTG CGC GAG CTG       391
Val Phe Gly Asp Leu Gly Cys Arg Gly Tyr Tyr Phe Val Arg Glu Leu
        105                 110                 115
```

```
TGC GCC TAC GCC ACA GTG CTG AGC GTT GCC AGC CTA AGC GCA GAG CGC        439
Cys Ala Tyr Ala Thr Val Leu Ser Val Ala Ser Leu Ser Ala Glu Arg
            120                 125                 130

TGC CTG GCC GTG TGC CAG CCG CTG CGC GCC CGC CGC CTT CTC ACC CCG        487
Cys Leu Ala Val Cys Gln Pro Leu Arg Ala Arg Arg Leu Leu Thr Pro
    135                 140                 145

CGC CGC ACC CGC CGC CTG CTG TCA CTG GTC TGG GTC GCC TCT CTG GGC        535
Arg Arg Thr Arg Arg Leu Leu Ser Leu Val Trp Val Ala Ser Leu Gly
150                 155                 160                 165

CTT GCC CTG CCC ATG GCG GTT ATC ATG GGA CAG AAG CAC GAA GTG GAA        583
Leu Ala Leu Pro Met Ala Val Ile Met Gly Gln Lys His Glu Val Glu
                170                 175                 180

AGC GCG GAC GGG GAG CCT GAG CCT GCC TCG CGT GTG TGC ACG GTG CTG        631
Ser Ala Asp Gly Glu Pro Glu Pro Ala Ser Arg Val Cys Thr Val Leu
            185                 190                 195

GTG AGC CGC GCC ACA CTT CAG GTC TTC ATC CAG GTG AAT GTG CTG GTG        679
Val Ser Arg Ala Thr Leu Gln Val Phe Ile Gln Val Asn Val Leu Val
        200                 205                 210

TCC TTC GCT CTC CCC TTG GCA CTC ACT GCT TTC CTG AAT GGC ATC ACT        727
Ser Phe Ala Leu Pro Leu Ala Leu Thr Ala Phe Leu Asn Gly Ile Thr
    215                 220                 225

GTC AAC CAC CTG ATG GCC CTC TAC TCC CAG GTA CCA TCA GCT TCT GCC        775
Val Asn His Leu Met Ala Leu Tyr Ser Gln Val Pro Ser Ala Ser Ala
230                 235                 240                 245

CAA GTC AGC TCC ATC CCC AGC CGC CTG GAG CTC CTG AGT GAG GAA GGC        823
Gln Val Ser Ser Ile Pro Ser Arg Leu Glu Leu Leu Ser Glu Glu Gly
                250                 255                 260

CTC CTG GGC TTC ATC ACG TGG AGA AAG ACT CTC TCC CTG GGG GTC CAA        871
Leu Leu Gly Phe Ile Thr Trp Arg Lys Thr Leu Ser Leu Gly Val Gln
            265                 270                 275

GCC AGC CTG GTG AGA CAC AAG GAT GCC AGC CAG ATC CGC AGC CTC CAG        919
Ala Ser Leu Val Arg His Lys Asp Ala Ser Gln Ile Arg Ser Leu Gln
        280                 285                 290

CAC AGC GCC CAG GTT CTC AGA GCC ATC GTG GCT GTG TAT GTC ATC TGC        967
His Ser Ala Gln Val Leu Arg Ala Ile Val Ala Val Tyr Val Ile Cys
    295                 300                 305

TGG CTG CCG TAC CAT GCC CGC CGA CTC ATG TAC TGC TAC ATC CCC GAT       1015
Trp Leu Pro Tyr His Ala Arg Arg Leu Met Tyr Cys Tyr Ile Pro Asp
310                 315                 320                 325

GAT GGA TGG ACT AAT GAG CTC TAT GAT TTC TAT CAC TAT TTC TAC ATG       1063
Asp Gly Trp Thr Asn Glu Leu Tyr Asp Phe Tyr His Tyr Phe Tyr Met
                330                 335                 340

GTG ACC AAC ACG CTC TTC TAT GTC AGC TCA GCA GTG ACC CCA ATC CTC       1111
Val Thr Asn Thr Leu Phe Tyr Val Ser Ser Ala Val Thr Pro Ile Leu
            345                 350                 355

TAC AAC GCC GTG TCT TCC TCC TTC AGA AAG CTC TTC CTG GAA TCC CTC       1159
Tyr Asn Ala Val Ser Ser Ser Phe Arg Lys Leu Phe Leu Glu Ser Leu
        360                 365                 370

GGC TCC CTG TGT GGT GAA CAG CAC TCC TTG GTG CCC TTA CCC CAA GAA       1207
Gly Ser Leu Cys Gly Glu Gln His Ser Leu Val Pro Leu Pro Gln Glu
375                 380                 385

GCC CCA GAG TCA ACC ACT AGT ACG TAC AGT TTC CGG CTT TGG GGA TCC       1255
Ala Pro Glu Ser Thr Thr Ser Thr Tyr Ser Phe Arg Leu Trp Gly Ser
                390                 395                 400                 405

CCA AGA AAC CCC AGC CTG GGA GAA ATA CAA GTA TGAAGAGAAC AAACAATG       1308
Pro Arg Asn Pro Ser Leu Gly Glu Ile Gln Val
                410                 415

TGCTTGGGAC ATGCCCGTCA GACAAGCCAT GCCATCACTA ACAGTCCAGG TGGACCTA       1368

GACCCAGTGC ATACTGCAGG CAAACCACAT AACACCTACT GCCCTCAGCT TCCCACAG       1428
```

AACAACAGAG TTGAAGAATA GGAACCGTGG CCTAGTGATG AAGGTGCCCA GTGCCAGG         1488

TGGTACATAG TCACTACTCA ATAAATTTTA ACCCGGTGCT G                          1529

(2) INFORMATION FOR SEQ ID NO: 4:

(i) SEQUENCE CHARACTERISTICS:
        (A) LENGTH: 416 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Glu Thr Ser Ser Pro Trp Pro Pro Arg Pro Ser Pro Ser Ala Gly
 1               5                  10                  15

Leu Ser Leu Glu Ala Arg Leu Gly Val Asp Thr Arg Leu Trp Ala Lys
            20                  25                  30

Val Leu Phe Thr Ala Leu Tyr Ser Leu Ile Phe Ala Phe Gly Thr Ala
        35                  40                  45

Gly Asn Ala Leu Ser Val His Val Leu Lys Ala Arg Ala Gly Arg
    50                  55                  60

Pro Gly Arg Leu Arg Tyr His Val Leu Ser Leu Ala Leu Ser Ala Leu
65                  70                  75                  80

Leu Leu Leu Leu Val Ser Met Pro Met Glu Leu Tyr Asn Phe Val Trp
                85                  90                  95

Ser His Tyr Pro Trp Val Phe Gly Asp Leu Gly Cys Arg Gly Tyr Tyr
            100                 105                 110

Phe Val Arg Glu Leu Cys Ala Tyr Ala Thr Val Leu Ser Val Ala Ser
        115                 120                 125

Leu Ser Ala Glu Arg Cys Leu Ala Val Cys Gln Pro Leu Arg Ala Arg
    130                 135                 140

Arg Leu Leu Thr Pro Arg Arg Thr Arg Arg Leu Leu Ser Leu Val Trp
145                 150                 155                 160

Val Ala Ser Leu Gly Leu Ala Leu Pro Met Ala Val Ile Met Gly Gln
                165                 170                 175

Lys His Glu Val Glu Ser Ala Asp Gly Glu Pro Glu Pro Ala Ser Arg
            180                 185                 190

Val Cys Thr Val Leu Val Ser Arg Ala Thr Leu Gln Val Phe Ile Gln
        195                 200                 205

Val Asn Val Leu Val Ser Phe Ala Leu Pro Leu Ala Leu Thr Ala Phe
    210                 215                 220

Leu Asn Gly Ile Thr Val Asn His Leu Met Ala Leu Tyr Ser Gln Val
225                 230                 235                 240

Pro Ser Ala Ser Ala Gln Val Ser Ser Ile Pro Ser Arg Leu Glu Leu
                245                 250                 255

Leu Ser Glu Glu Gly Leu Leu Gly Phe Ile Thr Trp Arg Lys Thr Leu
            260                 265                 270

Ser Leu Gly Val Gln Ala Ser Leu Val Arg His Lys Asp Ala Ser Gln
        275                 280                 285

Ile Arg Ser Leu Gln His Ser Ala Gln Val Leu Arg Ala Ile Val Ala
    290                 295                 300

Val Tyr Val Ile Cys Trp Leu Pro Tyr His Ala Arg Arg Leu Met Tyr
305                 310                 315                 320

Cys Tyr Ile Pro Asp Asp Gly Trp Thr Asn Glu Leu Tyr Asp Phe Tyr
                325                 330                 335
```

```
His Tyr Phe Tyr Met Val Thr Asn Thr Leu Phe Tyr Val Ser Ser Ala
            340                 345                 350

Val Thr Pro Ile Leu Tyr Asn Ala Val Ser Ser Ser Phe Arg Lys Leu
            355                 360                 365

Phe Leu Glu Ser Leu Gly Ser Leu Cys Gly Glu Gln His Ser Leu Val
        370                 375                 380

Pro Leu Pro Gln Glu Ala Pro Glu Ser Thr Thr Ser Thr Tyr Ser Phe
385                 390                 395                 400

Arg Leu Trp Gly Ser Pro Arg Asn Pro Ser Leu Gly Glu Ile Gln Val
                405                 410                 415
```

(2) INFORMATION FOR SEQ ID NO: 5:

(i) SEQUENCE CHARACTERISTICS:
    (A) LENGTH: 23
    (B) TYPE: nucleic acid
    (C) STRANDEDNESS: single
    (D) TOPOLOGY: linear (xi) SEQUENCE DESCRIPTION: SEQ ID NO: 5:

GATCCGGGCC CTTTTTTTTT TTT                     23

(2) INFORMATION FOR SEQ ID NO: 6:

(i) SEQUENCE CHARACTERISTICS:
    (A) LENGTH: 20
    (B) TYPE: nucleic acid
    (C) STRANDEDNESS: single
    (D) TOPOLOGY: linear (xi) SEQUENCE DESCRIPTION: SEQ ID NO: 6:

AAAAAAAAAA AAAGGGCCCG                      20

(2) INFORMATION FOR SEQ ID NO: 7:

(i) SEQUENCE CHARACTERISTICS:
    (A) LENGTH: 40
    (B) TYPE: nucleic acid
    (C) STRANDEDNESS: single
    (D) TOPOLOGY: linear (xi) SEQUENCE DESCRIPTION: SEQ ID NO: 7:

CAACTCAAGC TTGCCGCCAC CATGGAAACC AGCAGCCCGC          40

(2) INFORMATION FOR SEQ ID NO: 8:

(i) SEQUENCE CHARACTERISTICS:
    (A) LENGTH: 29
    (B) TYPE: nucleic acid
    (C) STRANDEDNESS: single
    (D) TOPOLOGY: linear (xi) SEQUENCE DESCRIPTION: SEQ ID NO: 8:

CCGCGAATTC TCAGGTCCGG GTTTCTGGG               29

(2) INFORMATION FOR SEQ ID NO: 9:

(i) SEQUENCE CHARACTERISTICS:
    (A) LENGTH: 18
    (B) TYPE: nucleic acid
    (C) STRANDEDNESS: single
    (D) TOPOLOGY: linear (xi) SEQUENCE DESCRIPTION: SEQ ID NO: 9:

-continued

```
CTGGCCCTCT GCTCCCAA                                              18

(2) INFORMATION FOR SEQ ID NO: 10:

(i) SEQUENCE CHARACTERISTICS:
        (A) LENGTH: 19
        (B) TYPE: nucleic acid
        (C) STRANDEDNESS: single
        (D) TOPOLOGY: linear (xi) SEQUENCE DESCRIPTION: SEQ ID NO: 10:

TCAGGTCCGG GTTTCTGGG                                             19

(2) INFORMATION FOR SEQ ID NO: 11:

(i) SEQUENCE CHARACTERISTICS:
        (A) LENGTH: 19
        (B) TYPE: nucleic acid
        (C) STRANDEDNESS: single
        (D) TOPOLOGY: linear (xi) SEQUENCE DESCRIPTION: SEQ ID NO: 11:

ATGGAAACCA GCAGCCCGC                                             19

(2) INFORMATION FOR SEQ ID NO: 12:

(i) SEQUENCE CHARACTERISTICS:
        (A) LENGTH: 22
        (B) TYPE: nucleic acid
        (C) STRANDEDNESS: single
        (D) TOPOLOGY: linear (xi) SEQUENCE DESCRIPTION: SEQ ID NO: 12:

TCATTCTTGC ATTACATTCA GG                                         22
```

TYPE-2 NEUROTENSIN RECEPTOR (NT-R2)

The present invention relates to a polypeptide which constitutes a subtype of the neurotensin receptor, known as the type-2 neurotensin receptor (NT-R2), in mammals.

Neurotensin (NT) is a tridecapeptide involved in intracellular communication. It acts as a hormone in peripheral organs and as a neurotransmitter in the central nervous system (Carraway R. et al., Peptides, 1982, 3, 115–123 and Maj. J. K. et al., Neuroscience, 1987, 22, 499–524). In particular, it modulates the transmission of dopamine in the nigrostriatal and mesolimbic pathways (Nemeroff, C.B., Psychoneuro-endocrinology, 1986, 11, 15–37 and Kitabgi, P., Neurochem. Int., 1989, 14, 111–119). In addition, NT plays a role in nociception, in hypothermia, in controlling the secretion of hypophyseal hormones and in muscle relaxation (Vincent, J. P., Cell. Mol. Neurobiol., 1995, 15, 501–512).

In adult rat brain, neurotensin binds at two distinct sites, which are distinguishable, on the one hand, by their sensitivity to levocabastine, an antagonist of the histamine H1 receptor, and, on the other hand, by their differential affinity for neurotensin (Schotte A. et al., Naunynschmiedeberg's Arch. Pharmacol., 1986, 333, 400–405). The low-affinity levocabastine-sensitive site appears after birth and has a distribution in the brain which is different from that of the high-affinity levocabastine-insensitive site (Schotte A. et al., Brain. Res., 1987, 408, 326–328).

The high-affinity levocabastine-insensitive receptor has been cloned from rat (Tanaka K. et al., Neuron, 1990, 4, 847–854) and from man (Vita N. et al., FEBS lett., 1993, 317, 139–142 and Watson M. et al., Mayo Clin. Proc., 1993, 68, 1043–1048). This receptor represents less than 30% of the NT binding sites in the adult rat brain; it has been found mainly in substantia nigra and in the ventral tegmental area. This cloned rat neurotensin receptor is a 424-amino-acid protein which belongs to the G-protein-coupled superfamily of receptors. The biochemical and pharmacological properties of this receptor have been studied extensively. It has been demonstrated that, upon activation, this receptor modulates the intracellular amount of cGMP (Amar S. et al., Biochem. Biophys. Res. Commun, 1985, 129, 117–125), of cAMP (Bozou J. C. et al., Biochem. J., 1989, 264, 871–878 and Yamada M. et al., Eur. J. Pharmacol., 1993, 244, 99–101) and of inositol phosphates (Watson M. A. et al., J; Neurochem., 1992, 59, 1967–1970 and Hermans E. et al., Mol. Pharmacol., 1996, 49, 365–372).

The recently discovered non-peptide NT antagonist, {2-[(1-(7-chloro-4-quinolinyl)-5-(2,6-di-methoxyphenyl)pyrazol-3-yl)carbonylamino]tricyclo-(3.3.1.1.3.7)decane-2-carboxylic} acid known under its code name SR 48692 and described in EP 477,049, inhibits the binding of NT to the cloned receptor (Gully D et al, Proc. Natl. Acad. Sci. USA, 1993, 90, 65–69) However, a recent study shows that in mice and in rats, the hypothermia and analgesia induced by NT are insensitive to SR 48692 (Dubuc I. et al., Br. J. Pharmacol., 1994, 112, 352–354), therefore suggesting that NT might act differently through different receptor subtypes.

It has also been demonstrated that SR 48692 may affect differently the NT-induced behaviour and changes in dopaminergic transmission (Poncelet M. et al., Naunynschmiedeberg's Arch. Pharmacol., 1994, 349, 57–60 and Steinberg R. et al., Neuroscience, 1994, 59, 921–929). Besides pharmacological arguments in favour of NT receptor subtypes, a recent study comparing the distributions of the neurotensin receptor and the transcripts of the cloned neurotensin receptor in rat brain has suggested the existence of another neurotensin receptor (Nicot A. et al., J. Comp. Neurol. 1994, 59, 921–929 and Le F. et al., Trends Pharmacol. Sci., 1996, 17, 1–3). The neurotensin receptor transcripts are detected in different regions of the brain, but not in the subfornical region, although the neurotensin binding sites have been clearly associated with the cell bodies of this region (Nicot A. et al., J. Comp. Neurol., 1994, 59, 921–929).

Moreover, a novel and very powerful neurotensin antagonist has recently been described (Gully et al.) 2-{(5-(2,6-dimethoxyphenyl)-1-(4-(N-(3-dimethylamino-propyl)-N-methylcarbamoyl)-2-isopropylphenyl)-1H-pyrazole-3-carbonyl)amino}adamantane-2-carboxylic acid hydrochloride, known under the code name SR 142948 A. This compound has an affinity of the order of a nanomole and completely displaces $[^{125}I]$-neurotensin and $[^3H]$-SR 48692 from their binding with the type-1 receptor (Gully et al.).

SR 142948 A antagonizes the effects in vitro (formation of IP1 in HT29 cells ($IC_{50}$=3.9 nM) or mobilization of intracellular calcium ions in CHO cells transfected with NT-1R) and in vivo of neurotensin (release of acetylcholine in rat striatum, hypothermia and analgesia in rats and mice, rotation in mice).

The inventors have demonstrated the existence of a novel neurotensin receptor subtype in mammals, known as the NT-R2 receptor. More particularly, they have managed to clone and sequence the NT-R2 receptor of rats (rNT-R2), (Chalon P., et al., FEBS Letters, 1996, 386, 91–94), and the human NT-R2 receptor (hNT-R2).

The inventors have also been able to study the pharmacological profile of the NT-R2 receptor: the NT-R2 receptor has a strong affinity for neurotensin as well as for xenine, neuromedin and levocabastine, is insensitive to the compound SR 48692 and binds the compound SR 142948 A strongly.

The NT-R2 receptor is a membrane protein consisting of seven transmembrane domains, preceded by a long extracellular amino-terminal domain and followed by a long intracellular carboxy-terminal domain. Hydropathic analysis of the NT-R2 according to the invention indicates eight hydrophobic regions of approximately 20 amino acids, corresponding to a potential signal peptide at the $NH_2$ end, plus seven transmembrane domains. After removal of the signal peptide, the receptor representing the invention has a molecular weight of approximately 40–45 kilodaltons.

The NT-R2 receptor is coupled in vivo to G proteins which allow transduction of the signal via the phospholipase C pathway.

The present invention thus relates to an isolated polypeptide which constitutes the type-2 neurotensin receptor (NT-R2).

More particularly, the invention relates to a purified polypeptide which constitutes the type-2 neurotensin receptor of rats (rNT-R2) and of man (hNT-R2).

More particularly, the subject of the invention is an hNT-R2 polypeptide comprising the amino acid sequence SEQ ID No. 2 or the amino acid sequence SEQ ID No. 4, or any polypeptide fragment or derivative thereof which is biologically active.

The sequence SEQ ID No. 2 represents the amino acid sequence of the hNT-R2 polypeptide. The seven potential transmembrane domains of the protein are underlined.

The sequence SEQ ID No. 4 represents the amino acid sequence of the rNT-R2 polypeptide.

The term "derivative" is understood to refer to any polypeptide variant of the polypeptide having the sequence SEQ ID No. 2 or No. 4 or any molecule resulting from a genetic and/or chemical modification of the sequence SEQ ID No. 2 or No. 4, that is to say obtained by mutation, deletion, addition, substitution and/or chemical modification of a single or of a limited number of amino acids, as well as any isoform sequence, that is to say a sequence which is identical to the sequence SEQ ID No. 2 or No. 4, to one of its modified sequences or fragments, containing one or more amino acids in the form of the D enantiomer, the said iso-form, modified or variant sequences having conserved at least one of the properties which makes them biologically active.

The expression "biologically active" means that the compound to which it refers is capable of binding to neurotensin or to ligands related to neurotensin and/or of participating in the transduction of the signal induced by neurotensin in the cell membrane, and/or capable of inducing antibodies which recognize the NT-R2 polypeptide according to the invention. The ligands related to neurotensin may be, in particular, molecules having at least 20% homology with the amino acid sequence of natural human neurotensin, or fragments or derivatives thereof. Examples of ligands related to neurotensin are xenopsine, xenine and neuromedin.

The invention thus comprises any polypeptide having an amino acid sequence which is substantially identical to the sequence ID No. 2 or No. 4 in which one or more residues have been conservatively replaced by a functionally similar residue and which demon-strates its ability to mimic the NT-R2 as described in the present invention. Examples of conservative replacements include the replacement of a hydrophobic residue such as isoleucine, valine, leucine or methionine by another hydrophobic residue, the replacement of a polar hydrophilic residue such as arginine by lysine, glutamine by asparagine or glycine by serine, the replacement of a basic residue such as lysine, arginine or histidine by another basic residue or the replacement of an acidic residue such as aspartic acid and glutamic acid by another acidic residue.

Similarly, the invention comprises any polypeptide having one or more residues which are derived chemically by reaction of a functional group. Such derived molecules include, for example, molecules in which the free amino groups have been substituted in order to form amine hydrochlorides, p-toluenesulphonyl groups, carbobenzoxy groups, tert-butyloxycarbonyl groups, chloroacetyl groups or formyl groups. The free carboxylic acid groups may be derived in order to form salts, methyl or ethyl esters or other types of esters or hydrazides. The free hydroxyl groups may be substituted in order to form O-acyl or O-alkyl derivatives. The imidazole nitrogen of the histidine may be substituted in order to form N-imidazolebenzylhistidine. Peptides which contain one or more derivatives of an amino acid in its natural form from the 20 natural amino acids are also included as chemical derivatives. For example, proline may be replaced by 4-hydroxyproline; lysine may be replaced by 5-hydroxylysine; histidine may be replaced by 3-methylhistidine; serine may be replaced by homoserine; and lysine may be replaced by ornithine. The polypeptides of the present invention also include any polypeptide having one or more additions and/or deletions of residues relative to the sequence ID No. 2 or No. 4 provided that the biological activity is maintained.

When other residues have either been added to an end for the purpose of providing an "acceptor" peptide by which the polypeptides of the invention may readily be attached to a label or to a solid matrix, or have been added to a support, the "acceptor" residues do not form epitopes of the NT-R2.

The acceptors may contain up to 40 residues or more, preferably from 1 to 10 residues. The common amino acid residues used for the binding are tyrosine, cysteine, lysine, glutamic acid and aspartic acid. In addition, a polypeptide of the invention may differ from the sequence SEQ ID No. 2 of hNT-R2 or from the sequence SEQ ID No. 4 of rNT-R2 by modification of the sequence, for example by N-terminal acylation, by acetylation or by reaction with thioglycolic acid, and by C-terminal amidation, for example with ammonia or methylamine.

The NT-R2 polypeptides of the present invention may be synthesized by all the methods which are well known to those skilled in the art, including recombinant DNA techniques. The NT-R2 polypeptides may be synthesized by synthetic chemistry techniques, such as Merrifield-type synthesis which is advantageous for reasons of purity, antigen specificity, absence of undesired side products and for its ease of production. A summary of the various techniques available may be found in J. M. Steward and J. D. Young, "Solid Phase Peptide Synthesis", W. H. Freeman Co., San Francisco, 1969; M. Bodansky et a., "Peptide Synthesis", John Wiley & Sons, second edition, 1976 and J. Meienhofer, "Hormonl Proteins and Peptides", 1983, 2, 46, Academic Press (New York), for the solid-phase synthesis of peptides, and in E. Schroder and K. Kubke, "The Peptides", 1965, 1, Academic Press (New York) for synthesis in conventional solutions. Suitable protecting groups which can be used in such a synthesis are described in the texts mentioned above and in J. F. W. McOmie, "Protective Groups in Organic Chemistry", Plenum Press, New York.

The subject of the invention is also the isolated nucleotide sequence selected from the sequence SEQ ID No. 1, the sequence SEQ ID No. 3, nucleotide sequences derived from the sequence ID No. 1 or No. 3 by degeneracy of the genetic code, mutation, deletion, insertion, a splice variant or an allelic variability, and nucleotide sequences capable of hybridizing specifically with the sequence ID No. 1 or with the sequence SEQ ID No. 3.

The various mammalian nucleotide sequences according to the invention may or may not be of artificial origin. They may be DNA or RNA sequences obtained by screening sequence libraries using probes developed on the basis of the sequence SEQ ID No. 1 or of the sequence SEQ ID No. 3. Such libraries may be prepared by standard techniques of molecular biology, which are known to those skilled in the art.

The nucleotide sequences according to the invention may also be prepared by chemical synthesis, or alternatively by mixed methods including chemical or enzymic modification of sequences obtained by screening libraries.

These nucleotide sequences allow the production of nucleotide probes which encode a polypeptide according to the invention or a biologically active fragment thereof. The appropriate hybridization conditions correspond to the temperature and ionic strength conditions usually used by those skilled in the art, preferably to temperature conditions of between ($T_m$ minus 5° C.) and ($T_m$ minus 30° C.) and, more preferably, to temperature conditions of between ($T_m$ minus 5° C.) and ($T_m$ minus 10° C.) (high stringency), $T_m$ between the theoretical melting point, defined as being the temperature at which 50% of the paired strands separate. Such probes also form part of the invention. They may be used as in vitro diagnostic tools for the detection, by hybridization experiments, of transcripts which are specific for the polypeptides of the invention in biological samples or for the revelation of aberrant syntheses or genetic anomalies resulting from a polymorphism, from mutations or from poor splicing.

The probes of the invention contain a minimum of 10 nucleotides and favourably at least 14 nucleotides, preferably at least 20 nucleotides and more preferably at least 50 nucleotides, and at the maximum contain all of the nucleotide sequence SEQ ID No. 1 or No. 3 or its complementary strand.

Preferably, the probes of the invention are labelled prior to their use. For this, several techniques are available to those skilled in the art, such as, for example, fluorescent, radioactive, chemoluminescent or enzymic labelling.

The in vitro diagnostic methods in which these nucleotide probes are used for the detection of aberrant syntheses or genetic anomalies, such as the loss of heterozygosity and genetic rearrangement, in nucleic acid sequences encoding an NT-R2 polypeptide or a biologically active fragment, are included in the present invention. A method of such type comprises:

placing a nucleotide probe of the invention in contact with a biological sample under conditions which allow the formation of a hybridization complex between the said probe and the said nucleotide sequence contained in the biological sample, optionally after a prior step of amplification of the said nucleotide sequence;

detecting the hybridization complex which is possibly formed;

optionally, sequencing the nucleotide sequence forming the hybridization complex with the probe of the invention.

The cDNA probes of the invention can also advantageously be used for the detection of chromosomal anomalies.

The nucleotide sequences of the invention are also useful for the manufacture and use of sense and/or antisense oligonucleotide primers for sequencing reactions or for specific amplification reactions according to the so-called PCR (polymerase chain reaction) technique or any other variant thereof.

The nucleotide sequences according to the invention moreover have therapeutic uses, for the production of antisense sequences which are capable of hybridizing specifically with a nucleic acid sequence, including a messenger RNA, and which can be used in gene therapy. Thus, the subject of the invention is antisense sequences which are capable of inhibiting, at least partially, the production of NT-R2 polypeptides as defined above. Such sequences consist advantageously of those which constitute the reading frame encoding NT-R2 in the transcript.

The nucleotide sequences according to the invention may moreover be used for the production of recombinant polypeptides having NT-R2 receptor activity as defined above.

These polypeptides may be produced from nucleotide sequences defined above, according to techniques for the production of recombinant products which are known to those skilled in the art.

According to one embodiment of the invention, the nucleotide sequence may be inserted into an expression vector, in which it is linked operatively to components which allow its expression to be regulated, in particular such as transcription promoters or terminators.

Such an expression vector may be, in particular, a plasmid, a phage or any type of recombinant virus.

Among the prokaryotic transformation vectors which are well known to those skilled in the art, mention may be made of the ZAP Lambda phage vector and the pBluescript plasmid (Stratagene). Other vectors which are suitable for the transformation of E.coli cells include pET expression vectors (Novagen, cf. U.S. Pat. No. 4,952,496) for example, pET11a, which contains the T7 promoter, the T7 terminator, the E.coli inducible Lac operon and the Lac repressor gene; and pET 12a–c, which contains the T7 promoter, the T7 terminator and the E.coli omPT secretion signal.

The vectors which are particularly preferred for the transfection of mammalian cells are vectors containing the cytomegalovirus (CMV) promoters such as pcDNA1 (Invitrogen), vectors containing the MMTV promoter such as pMAMNeo (Clontech) and pMSG (catalogue No. 27-4506-01 from Pharmacia) and vectors containing the SV40 promoter such as pSVβ (Clontech).

In the present invention, a promoter refers to a DNA segment which controls the transcription of DNA to which it is operatively attached. The promoter region includes specific sequences which are sufficient for recognition of the RNA polymerases, for binding and the initiation of transcription. In addition, the promoter region includes sequences which modulate this recognition, and the initiation of the binding and of the transcription of the RNA polymerase activity. As examples of promoters considered for use in the experiments according to the present invention, mention may be made of the SV40 promoter, the cytomegalovirus promoter, the mouse mammary tumour virus promoter (induced by steroids) and the Maloney murine leukaemia virus promoter.

The signals controlling the expression of the polypeptides (promoters, activators, termination sequences, etc.) are chosen as a function of the host cell used. To this end, the nucleotide sequences according to the invention may be inserted into autonomous replication vectors in the host chosen, or into vectors which integrate into the host chosen. Such vectors will be prepared according to the methods commonly used by those skilled in the art, and the clones resulting therefrom may be introduced into a suitable host by standard methods such as, for example, electroporation.

The expression vectors as described above, containing at least one of the nucleotide sequences defined according to the invention, also form part of the present invention.

The invention is moreover directed towards host cells transfected with these expression vectors. These cells may be obtained by introducing into host cells a nucleotide sequence which is inserted into a vector as defined above, followed by culturing the said cells under conditions which allow the replication and/or expression of the transfected nucleotide sequence.

Examples of host organisms include bacteria (for example E.coli), yeasts (for example Saccharomyces cerevisiae, Candida tropicalis, Hansenula polimorpha and P. pastoris; see for example U.S. Pat. Nos. 4,882,279, 4,837,148, 4,929,555 and 4,885,231), mammalian cells (for example HEK293, CHO, CV-1 and Ltk cells) and insect cells.

The host cells for expressing the functional recombinant NT-R2 receptor preferably express endogenous or recombinant G proteins.

G proteins are a highly conserved family of membrane-associated proteins composed of α, β and γ subunits. The α subunit which binds to GDP and GTP differs in the various G proteins. In its active form, the α subunit, bound to GTP, dissociates from the βγ complex and the subunits act specifically with each other with cell effector molecules in order to bring about a cellular response. Since different G proteins may interact with different effector systems (for example the phospholipase C pathway and the adenylate cyclase pathway), it is useful to investigate different host cells for the expression of different subtypes of recombinant NT-R2. Alternatively, the host cells may be transfected with DNA encoding G protein subunits for the heterologous expression of different G proteins.

The host cells expressing the NT-R2 receptor which are used for these biological tests may be, in particular, CHO cells and COS cells which are transformed by an expression vector as defined above. The expression vectors used may be, for example, plasmids containing in particular an SV40 origin of replication and optionally a reporter gene and/or a marker gene.

The host cells according to the invention can be used in a process for the production of an NT-R2 polypeptide, in which process cells transfected according to the invention are cultured under conditions allowing the expression of a polypeptlde having the sequence SEQ ID No. 2 or No. 4, or any biologically active fragment, homologue or derivative thereof, and the said biologically active polypeptide, fragment, derivative or homologue thereof is recovered and purified.

The purification processes used are known to those skilled in the art. The recombinant polypeptide obtained may be purified from cell lysates and extracts or from the supernatant of the culture medium, by methods used individually or in combination, such as fractionation, chromatography methods, immunoaffinity techniques using specific mono- or polyclonal anti-bodies, etc.

The mono- or polyclonal antibodies capable of specifically recognizing the NT-R2 receptor also form part of the invention.

Polyclonal antibodies may be obtained from the serum of an animal which has been immunized against the NT-R2 receptor according to the usual procedures.

According to one embodiment of the invention, a suitable synthetic peptide fragment to which a tyrosine residue has been added at the C-terminal end so as to couple it to bovine serum albumin (BSA) via a bisdiazo benzidine linkage by reaction for 2 hours at 4° C. may be used as antigen. The reaction mixture is dialysed in order to remove the low molecular weight fractions, and the residue is cooled in liquid nitrogen and stored at −20° C. Three-month-old white New Zealand rabbits are immunized with the equivalent of 1 mg of the peptide antigen according to the procedure described by Benoit et al., PNAS USA, 1982, 79, 917–921. At four-weekly intervals, the animals are treated by injections of 200 μg of antigen and are bled 10 to 14 days later. After the third injection, the antiserum is examined in order to determine its capacity to bind to the anti-genic peptide radiolabelled with iodine, prepared by the chloramine-T method, and is then purified by chromatography on a CMC ion exchange column. The antibody molecules are then collected from the mammals and isolated to the desired concentration by methods which are well known to those skilled in the art, for example using DEAE Sephadex® in order to obtain the IgG fraction.

In order to increase the specificity of the polyclonal serum, the antibodies may be purified by an immunoafifinity chromatography using immunizing polypeptides on a solid phase. The antibody is placed in contact with the immunizing polypeptide on a solid phase for a sufficient period so as to immunoreact the polypeptide with the antibody molecule in order to form an immunological complex on the solid phase.

Monoclonal antibodies may be obtained according to the standard method for culturing hybridomas which is described by Köhler and Milstein (Nature (1975) p. 195).

Particularly advantageous antibodies are antibodies directed against the extracellular domain of the NT-R2 receptor.

The antibodies according to the invention are, for example, chimeric antibodies, humanized antibodies and Fab and F(ab')2 fragments. They may also be in the form of labelled antibodies or immunoconjugates. For example, they may be combined with a toxin, such as diphtheria toxin, or with a radioactive product. These immunotoxins may, in this case, constitute therapeutic agents which can be used for the treatment of certain pathologies which involve overexpression of the NT-R2 receptor.

The antibodies of the invention, in particular the monoclonal antibodies, may also be used for the immunohistochemical analysis of the NT-R2 receptors on slices of specific tissues, for example by immunofluorescence, gold-labelling, immunoperoxidase, etc.

The anti-NT-R2 antibodies according to the present invention may also be used in therapeutic methods on mammals, preferably on humans, as an NT-R2 receptor agonist or antagonist, in order to neutralize or modulate the effect of the NT-R2, to increase the amount of free NT (for example NT not bound to an NT-R2 receptor) or to increase the level of second messengers.

The anti-NT-R2 antibodies may advantageously be used in any situation in which expression of the NT-R2 receptor must be observed (abnormal overexpression, followed by regulation of the membrane expression, etc.).

The invention thus also relates to a method for the in vitro diagnosis of an abnormal accumulation or expression of NT-R2 receptor in a biological sample and/or for measuring the level of expression of this receptor in the said sample, which comprises placing at least one antibody as defined above in contact with the said biological sample under conditions which allow the possible formation of specific immunological complexes between an NT-R2 receptor and the said antibody or antibodies, and detecting the specific immunological complexes which are possibly formed.

The subject of the invention is also a kit for the in vitro diagnosis of an abnormal expression of the NT-R2 receptor in a biological sample and/or for measuring the level of expression of the NT-R2 receptor in the said sample, which comprises:
  at least one antibody which is specific for the NT-R2 receptor, optionally bound to a support,
  means for revealing the formation of specific antigen/ antibody complexes between the NT-R2 receptor and the said antibody and/or means for quantifying these complexes.

The subject of the invention is also a process for screening compounds which are capable of binding to the NT-R2 polypeptide according to the invention, in which the said compounds are placed in contact with the said NT-R2 polypeptide and the level of binding between the said compounds and the said NT-R2 polypeptide is evaluated.

A large number of compounds may thus be screened rapidly in order to test the capacity of these compounds to bind to the NT-R2 receptor according to the invention.

These binding tests may also be applied to the determination of the presence or absence of neurotensin in a biological sample, as well as to the isolation of novel endogenous ligands.

The subject of the invention is thus also a method for the in vitro diagnosis of an abnormal accumulation or expression of neurotensin or of analogues thereof in a biological sample and/or for measuring the level of expression thereof in the said sample, which comprises placing a polypeptide according to the invention in contact with the said biological sample under conditions which allow the formation of specific immunological complexes between the said polypeptide and the neurotensin or analogues thereof, and detecting the specific immunological complexes formed.

These binding tests may be carried out according to methods which are well known to those skilled in the art. The compounds capable of binding to the receptor polypeptide may, in particular, be labelled beforehand and may be used alone or in competition with other unlabelled compounds.

More particularly, competitive binding tests and ELISA or IRMA type tests may be carried out, for example.

Within the context of the invention, labelling means may be used in order to detect the NT-R2 receptor polypeptide according to the invention, the anti-NR-R2 antibodies and/or the NT-R2 receptor ligands.

The labelling means used may be, in particular, a fluorescent labelling agent which binds chemically to antibodies or to antigens without denaturation in order to form a fluorochromic dye which is a useful immunofluorescent indicator. Suitable fluorescent labelling agents may be fluorochromes such as fluoroscein isocyanate (FIC), fluoroscein isothiocyanate (FITC), 5-dimethylamino-1-naphthalenesulphonyl chloride (DANSC), tetramethylrhodamine isothiocyanate (TRITC), lissamine and rhodamine 8200 sulphonyl chloride (RB-200-SC). A description of the analytical techniques of immunofluorescence may be found in DeLuca "Immunofluorescence Analysis" and in Marchalonis et al., "Antibody as a Tool", 1982, 189–231, eds. John Wiley & Sons, Ltd.

The labelling agent may also be an enzyme, such as peroxidase (HRP) or glucose oxidase.

Radioactive elements may be used as labelling agents. A reference radiolabelling agent is a radio-active element which produces gamma-ray emissions. Elements which emit gamma rays, such as $^{124}I$, $^{126}I$, $^{131}I$ and $^{51}Cr$, represent a class of radioactive element indicator groups. $^{125}I$ is particularly preferred. Another group of labelling means which is useful consists of elements such as $^{11}C$, $^{18}F$, $^{15}O$ and $^{13}N$ which emit positrons. The positrons thus emitted produce gammarays when they encounter electrons present in the animal's body. Beta radiation, such as $^{32}P$, $^{111}In$ or $^{3}H$, is also useful.

The binding of a label to a substrate, that is to say the labelling of nucleic acid probes, antibodies, polypeptides or antibody molecules, is well known to those skilled in the art. For example, the antibody molecules may be labelled by metabolic incorporation of radiolabelled amino acids which are present in the culture medium. See for example Gaffre et al., Meth. Enzymol., 1981, 73, 3–46. The conventional means for conjugating or binding proteins by the activation of functional groups are particularly suitable. See for example Aurameas et al., Scand. J. Immunol. 1978, 8, Suppl. 7, 7–23, Rodwell et al., Biotech., 1984, 3, 889–894 and U.S. Pat. No. 4,493,795.

The subject of the invention is also a process for evaluating the pharmacological properties of compounds capable of binding to the NT-R2 receptor polypeptide, known as NT-R2 receptor ligands, which comprises the steps consisting in:
a) culturing cells which express the NT-R2 polypeptide, in the presence of at least one NT-R2 receptor ligand; and
b) evaluating the capacity of the ligand to modulate the transduction of the signal.

The NT-R2 receptor of the invention is, in its functional form, coupled to heterotrimeric G proteins. The G proteins combine with the transmembrane receptors on the intracellular side of the plasma membrane, the various α subunits of the G protein stimulating or inhibiting specific effectors. The specificity of the transduction of the signal may thus be determined by the specificity of the coupling G protein.

Thus, the capacity of a ligand to modulate the transduction of the signal may be evaluated by determining the concentration of intracellular cAMP formed by the activation of adenylate cyclase, and/or the intracellular concentration of inositol phosphates and of calcium which are produced by the activation of the phospholipase C pathway.

According to another embodiment of the invention, the capacity of a ligand to modulate the transduction of the signal may be evaluated by monitoring the expression of gene(s) induced by activation or inactivation of the NT-R2 receptor.

To this end, cells which express NT-R2 may advantageously be transformed with a reporter gene which is linked operatively to the said gene(s) whose transcription is induced by activation or inactivation of the NT-R2 receptor. After culturing these cells in the presence of at least one NT-R2 receptor ligand, the capacity of this ligand to modulate the transduction of the signal may be evaluated by monitoring the expression of the said reporter gene.

According to a variant of this embodiment, the said cells may advantageously be cultured in the presence:
either of increased concentrations of at least one NT-R2 receptor ligand whose capacity to modulate the transduction of the signal is desired and of a determined concentration of at least one known NT-R2 agonist;
or of increased concentrations of at least one known NT-R2 agonist and of a determined concentration of at least one NT-R2 receptor ligand whose capacity to modulate the transduction of the signal is desired.

The capacity of the said ligand to modulate the transduction of the signal is then evaluated by quantitatively determining the expression of the said reporter gene as a function of the concentration of the said ligand.

The biological tests according to the invention as are described above thus make it possible to evaluate the pharmacological profile of the compounds tested, in particular to determine whether the compounds tested are capable of acting as agonists or antagonists of the NT-R2 receptor according to the invention.

The present invention also relates to a pharmaceutical composition comprising an NT-R2 receptor polypeptide, a polypeptide fragment or a derivative thereof which is biologically active, an isolated nucleotide sequence selected from sequence ID No. 1 or sequence ID No. 3, nucleotide sequences derived from sequence ID No. 1 or No. 3 by degeneracy of the genetic code, mutation, deletion, insertion, a splice variant or an allelic variability, nucleotide sequences capable of hybridizing specifically with sequence ID No. 1 or No. 3, or an antibody directed against an NT-R2 receptor polypeptide, in combination with a pharmaceutically acceptable vehicle.

Lastly, the invention relates to the use of an NT-R2 polypeptide, polypeptide fragment or derivative, a nucleotide sequence or an antibody as are described above for the manufacture of a medicine intended to treat hormonal or neurological disorders in which the natural NT-R2 receptor and/or neurotensin is involved, these disorders being associated in particular with the overexpression of neurotensin and/or the exacerbated stimulation of the NT-R2 receptor, in mammals and in particular in man.

More particularly, such medicines may be useful in the treatment of thermoregulatory disorders, tension, disorders associated with muscle contraction, in particular the smooth muscle of the digestive tract, and in the treatment of pain.

An NT-R2 polypeptide according to the invention may be useful in particular for the manufacture of medicines with an analgesic and/or hypothermic effect.

The medicines according to the invention may also be useful for acting on the dopaminergic system and for treating neurological pathologies such as schizophrenia.

A pharmaceutical composition according to the invention may be administered via the oral, parenteral, intravenous, intramuscular, subcutaneous or percutaneous route or by intranasal or intracerebroventricular administration.

The preparation of pharmaceutical compositions which contain active principles dissolved or dispersed therein is well known to those skilled in the art. Generally, these compositions are prepared in the form of injectable suspensions or solutions. However, they may also be in solid forms which are suitable for preparing solutions or suspensions at the time of use. The preparations may also be emulsified.

The active principle may be mixed with excipients which are pharmaceutically acceptable and compatible with the active principle in an appropriate amount. Suitable excipients may be, for example, water, a saline solution, dextrose, glycerol or ethanol, as well as combinations of two or more of these. In addition, where appropriate, the compositions may contain minor amounts of auxiliary substances such as humidifying or emulsifying agents, and pH buffers which improve the efficacy of the active principle.

The therapeutic composition of the present invention may include pharmaceutically acceptable salts of the components of this invention. Pharmaceutically acceptable non-toxic salts include salts of addition to acids (formed with the free amino acid group of the polypeptide) which are formed with inorganic acids such as, for example, hydrochloric acid, hydrobromic acid, perchloric acid, nitric acid, thiocyanic acid, sulphuric acid, phosphoric acid, acetic acid, propionic acid, glycolic acid, lactic acid, pyruvic acid, oxalic acid, malonic acid, succinic acid, maleic acid, fumaric acid, anthranilic acid, cinnamic acid, napthalenesulphonic acid and sulphanilic acid.

Other pharmaceutically acceptable non-toxic salts include the salts of addition to bases. The salts formed with the free carboxyl groups may thus be derived from inorganic bases such as, for example, sodium hydroxide, ammonium hydroxide or potassium hydroxide, and from organic bases such as mono-, di-, tri-alkyl and aryl amines (for example triethylamine, diisopropylamine, methylamine and dimethylamine) and ethanolamines which are optionally substituted.

The modes of administration, the dosages and the pharmaceutical forms of the pharmaceutical compositions according to the invention may be determined according to the criteria generally taken into account when establishing a therapeutic treatment adapted to a patient, such as, for example, the age or the body-weight of the patient, the seriousness of his or her general state, the tolerance to the treatment, the side effects observed, etc.

The examples and figures, the key to which follows, illustrate the invention without limiting it.

KEY TO FIGURES

FIGS. 1a and 1b illustrate the pharmacological characteristics of rNT-R2 which is transiently expressed in COS-7 cells. FIG. 1a represents the saturation curve of $[^{125}I]$-NT on COS-7 cells expressing the rNT-R2 receptor. The Scatchard transformation of these data is given in the inserted graph. FIG. 1b gives the results of the displacement of $[^{125}I]$-NT by neurotensin (black circle), neuromedin N (white triangle), levocabastine (black square) and SR 48692 (black triangle). The data are obtained from a representative experiment which is repeated at least three times.

FIG. 2 illustrates the comparison of the amino acid sequences of the hNT-R1 receptor (Vita N. et al., FEBS lett., 1993 317, 139–142) and of the hNT-R2 receptor.

FIGS. 3a and 3b illustrate the pharmacological characteristics of the hNT-R2 which is transiently expressed in the COS-7 cells. FIG. 3a represents the saturation curve of $[^{125}I]$-NT on COS-7 cells expressing the hNT-R2 receptor. Scatchard transformation of these data is given in the inserted graph. FIG. 3b gives the results of the displacement of $[^{125}I]$-NT by neurotensin (black circle), xenine (white triangle), levocabastine (black square), SR 48692 (black triangle), and SR 142948 (white circle). The data are obtained from a representative experiment which is repeated at least 3 times.

FIG. 4b illustrates the tissue distribution of the hNT-R2 receptor.

FIGS. 5a–d illustrate the production of a CHO line which expresses the hNT-R2 receptor in a stable manner.

a) Structure of the plasmid used, b) Selection of the clones and subclones, c) Saturation curve of $[^{125}I]$-NT on CHO cell lines expressing the hNT-R2 receptor in a stable manner; Scatchard transformation of these data is given in the inserted graph, d) Displacement of $[^{125}I]$-NT by neurotensin (black circle), xenine (white triangle), levocabastine (black square), SR 48692 (black triangle) and SR 142948 (white circle). The data are obtained from a representative experiment which is repeated at least three times.

Figure 6A:
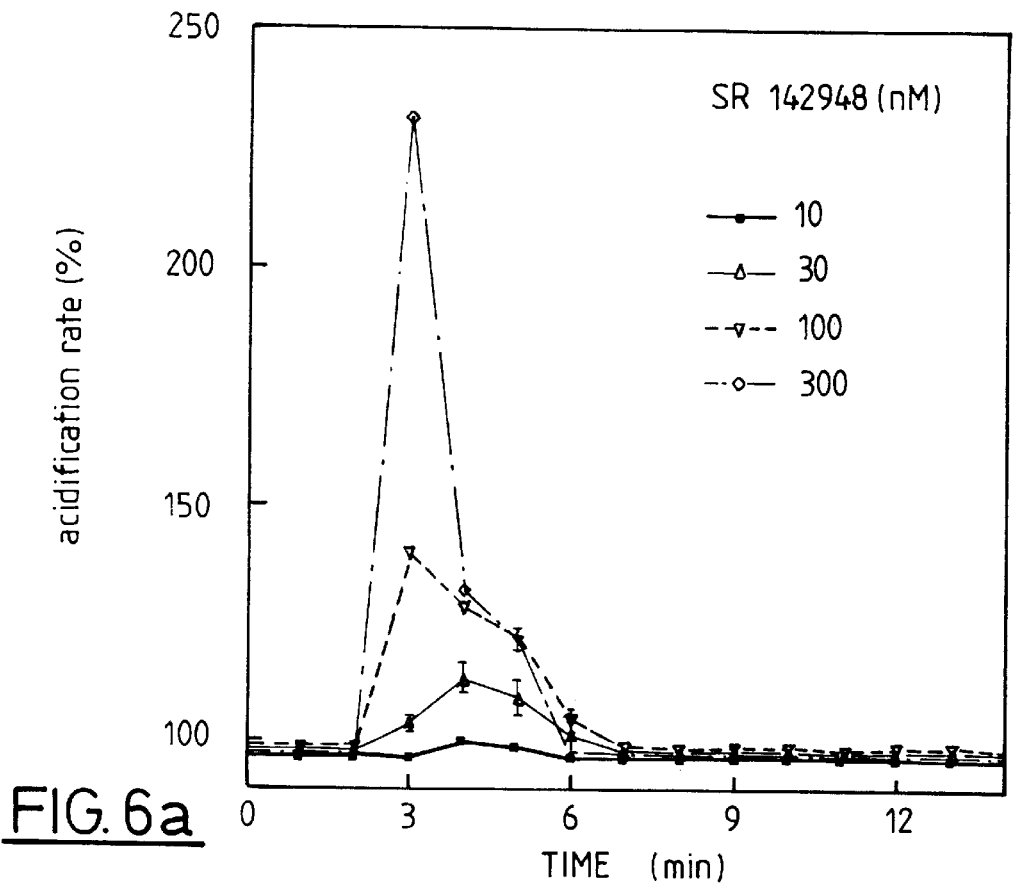
Figure 6B:
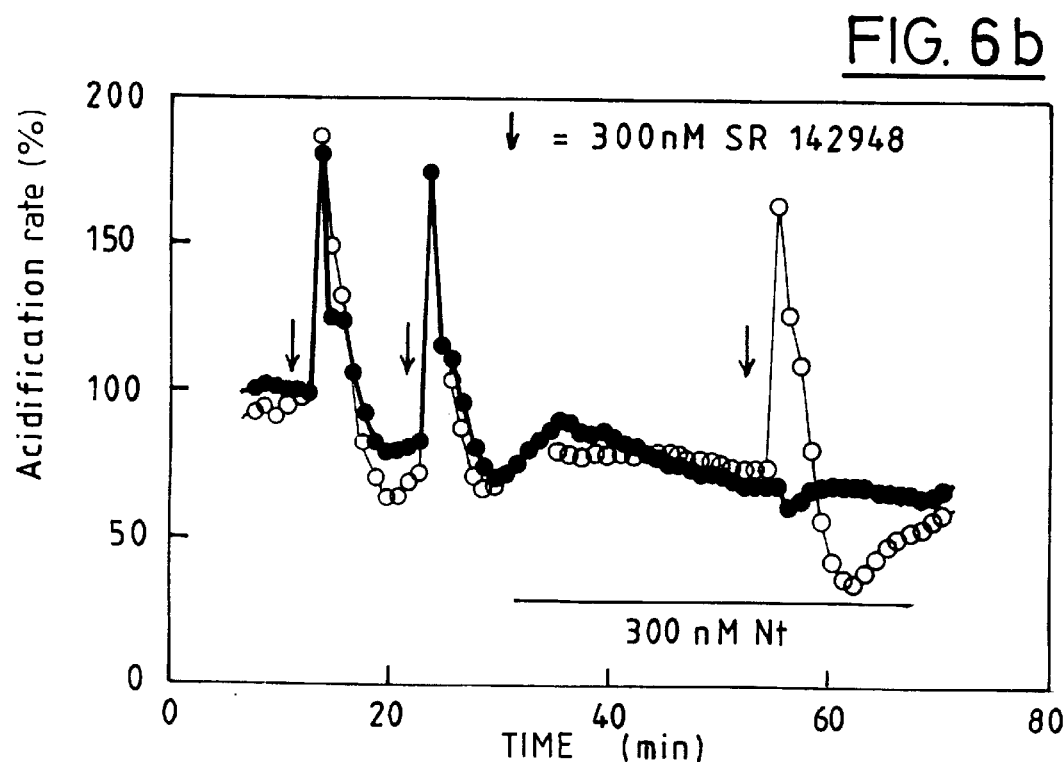

FIGS. 6a–b illustrate the microphysiometry experiments carried out with the CHO-hNT-R2 cells.

a) response dose of SR 142948, b) inhibition of the response of SR 142948 by neurotensin.

Example 1

Cloning of the cDNA of rNT-R2

1. Preparation of the Messenger RNA

Total RNA is extracted from rat hypothalamus using the acid guanidinium isothiocyanate phenol chloroform method (Chomczynski et al., 1987, Anal. Biochem. 162, 156–159). The polyadenylated RNA is isolated from the total RNA by chromatography on oligo(dT)cellulose. The RNA is separated by electrophoresis on 1% agarose/formaldehyde gel and then transferred onto nitrocellulose membranes. Hybridization with $^{32}P$-labelled NT-R1 cDNA is carried out under low stringency conditions.

2. Construction of the complementary DNA library and DNA sequencing:

The cDNA library is constructed using the "primer-adapter" procedure (Caput et al, 1986, Proc. Natl. Acad. Sci. USA, 83, 1670–1674) and the pT3-T7 vector (Pharmacia). About half a million recombinant bacteria were plated out at high density on filters and subjected to hybridization with the cDNA of labelled NT-R1.

The DNA sequences of the positive clones were determined by the Sanger method.

A cDNA of 1539 base pairs was isolated. It contains an open reading frame encoding a 416-amino-acid protein.

This rNT-R2 protein shows 43% identity and 64% homology with the rNT-R1 protein, and has the structural features of a G-protein-coupled receptor. It is interesting to note that, although the sizes of both proteins are similar, the new rNT-R2 receptor has a shorter N-terminal extracellular region and a longer intracytoplasmic loop between the 5th and 6th transmembrane domains. The cytoplasmic C-terminal region shows the lowest homology to NT-R1.

Example 2

Pharmnacological Characteristics of rNT-R2.

1. Materials and Methods:

$^{125}$I-[Tyr$^3$]-labelled neurotensin and unlabelled neurotensin are marketed by NEN and Sigma, respectively. BSA (bovine serum albumin), PMSF (phenylmethylsulphonyl fluoride) and 1,10-phenanthroline are marketed by Sigma. The selective, non-peptide antagonist SR 48692 was synthesized by Sanofi Recherche, France. Levocabastine was obtained from Janssen Pharmaceutica.

The pharmacological characterization was carried out using COS-3 cells transfected with pSVL-rNT-R2 recombinant vector. Three days after transfection, the cell monolayers were washed twice with 50 mM Tris-HCl pH 7.5, 0.1% BSA, 0.1% NaN$_3$, 1 mM 1,10-phenanthroline (binding buffer) before binding to the radioligand.

Saturation experiments were carried out in 1 ml of binding buffer containing $^{125}$I-neurotensin over a range from 0.05 to 14.5 nM. After incubation for one hour at room temperature, the medium was aspirated and the cell monolayers were washed twice with the incubation buffer. Finally, the cells were solubilized with 1 ml of 1N NaOH and the bound radioactivity was evaluated. The non-specific binding was defined as being the binding in the presence of a (500-fold) excess of unlabelled ligand and, under these conditions, was less than 1% of the total radioactivity.

Displacement experiments were conducted in a similar manner using 0.2 nM $^{125}$I-neurotensin as radioligand. The neurotensin, neuromedin N, SR 48692 and levoscabastine were used as competitors.

Figure 1A:
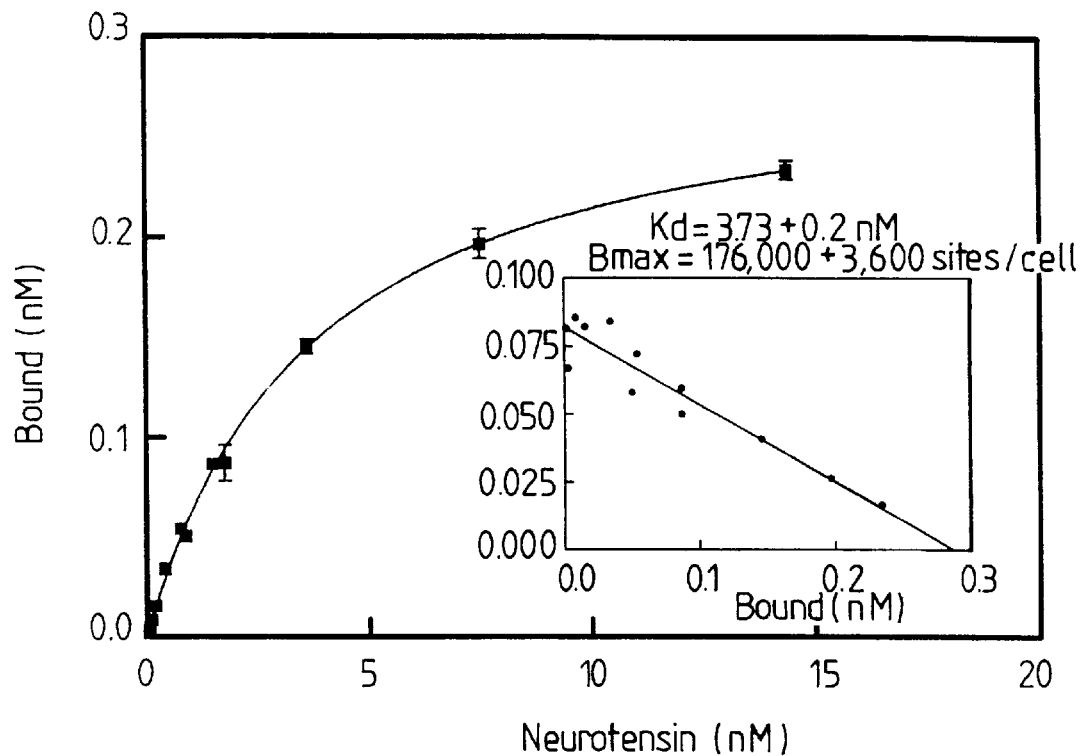
Figure 1B:
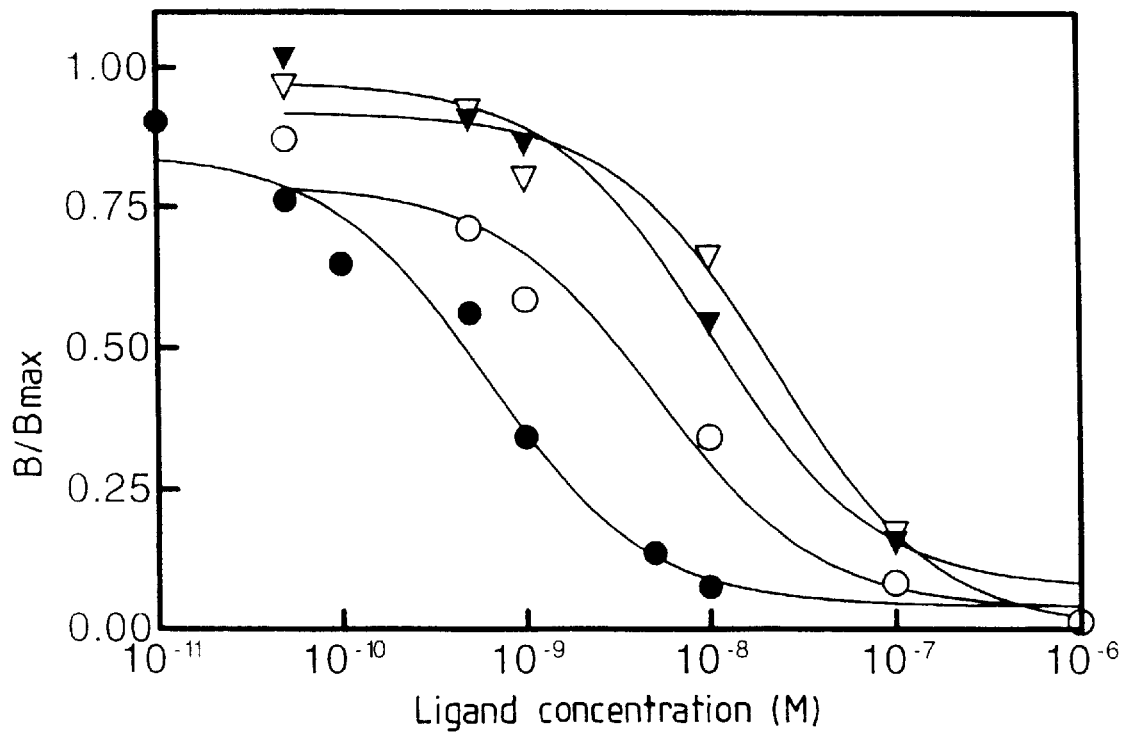
Figure 3A:
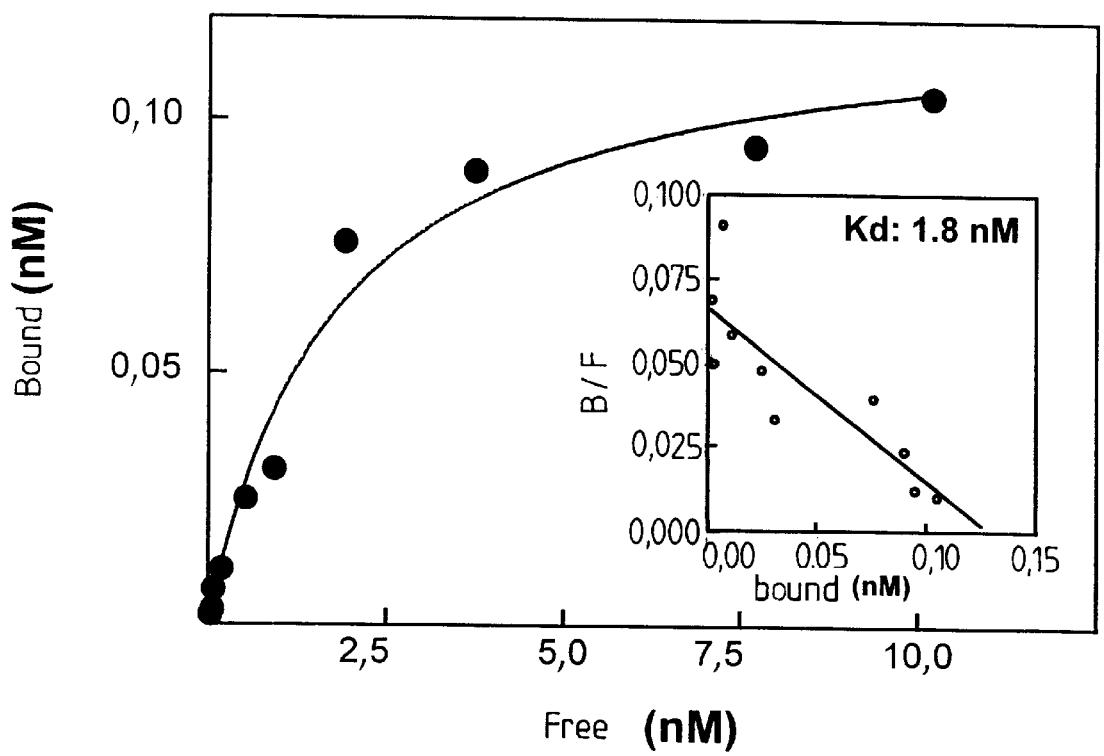
Figure 3B:
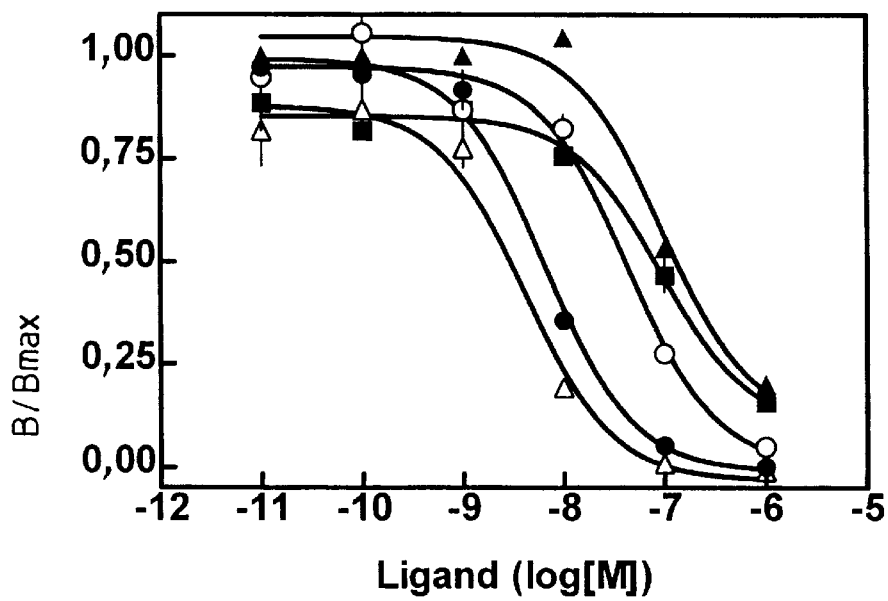
Figure 4A:
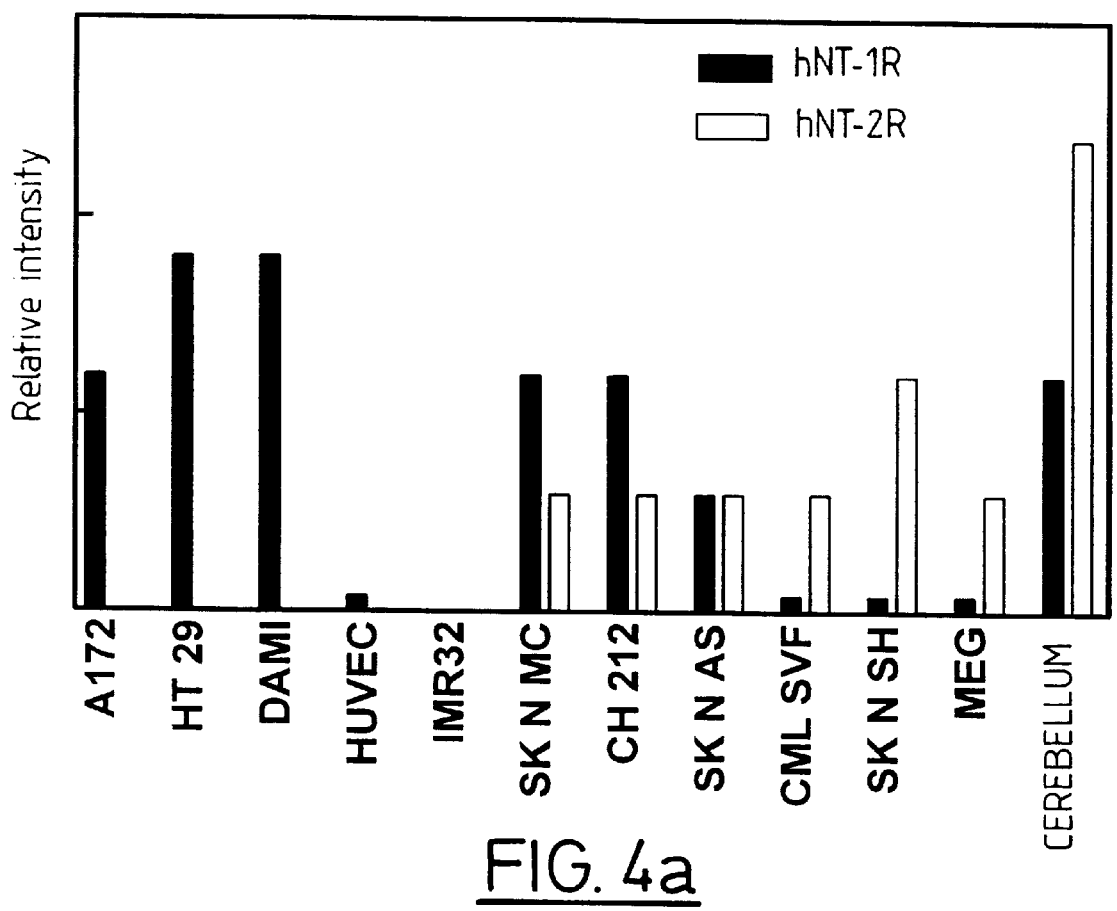
FIG. 4a illustrates the cell distribution of the hNT-R2 receptor in comparison with the hNT-R1 receptor on different cell lines of human origin.

2. Results:

The binding properties of neurotensin to the rNT-R2 receptor expressed in COS-3 cells after transfection of the cloned cDNA were studied. The receptor is able to bind $^{125}$I-neurotensin in a specific and saturable manner. Radiolabelled neurotensin did not bind to untransfected cells, or to cells transfected with the DNA vector alone. Scatchard analysis of the binding of $^{125}$I-neurotensin (FIG. 1a) shows a single high-affinity population of receptors with a dissociation constant (Kd) of 3.7±0.2 nM and a binding capacity (Bmax) of 180,000±3000 sites per cell.

FIG. 2b shows the competition curves of various ligands with radiolabelled neurotensin. The agonists and antagonists compete with the binding of $^{125}$I-neurotensin with an order of potency similar to that described for the NT-R1 receptor with the exception of the high affinity of levocabastine (Vita et al., 1993, FEBS Letters, 317, 139–142). Neurotensin is the most potent competitor, with an apparent IC$_{50}$ of 0.77 nM, followed by neuromedin N with an IC$_{50}$ of 5.1 nM, and levocabastine, with an IC$_{50}$ of 10.0 nM. The antagonist SR 48692 shows an IC$_{50}$ of 22.5 nM.

Example 3

Tissue Distribution of rNT-R2 mRNA.

The tissue distribution of rNT-R2 mRNA was examined by Northern blot analysis. Hybridization of the polyadenylated RNA obtained from the cortex and from the hypothalamus with labelled NT-R2 cDNA gives a strong signal. Weaker signals were also obtained with RNA from heart and intestine, which would suggest the involvement of the neurotensin/NT-R2 pathway in muscle function. Two transcripts were systematically detected, with sizes of 1.6 and 1.4 kb. The shorter transcript originates from a splice variant encoding a C-terminal-truncated receptor.

No transcript was detected in pituitary gland, spleen and kidney, using RT-PCR analysis.

Example 4

Cloning of hNT-R2 cDNA

1. Preparation of the Messenger RNA a) Extraction of the Messenger RNA.

Frozen cortex (obtained from adult human brain taken post-mortem) is pounded into powder.

The cell pellet is suspended in lysis buffer of the following composition: 4 M guanidine thiocyanate; 25 mM sodium citrate pH 7; 0.5% sarcosyl, 0.1 M β-mercaptoethanol. The suspension is sonicated using an Ultra Turrax No. 231256 sonicator (Janke and Kundel) at maximum power for one minute. Sodium acetate pH 4 is added to 0.2 M. The solution is extracted with one volume of a phenol/chloroform mixture (5/1 v/v). The RNA contained in the aqueous phase is precipitated at −20° C. using one volume of isopropanol. The pellet is resuspended in the lysis buffer. The solution is again extracted with a phenol/chloroform mixture and the RNA is precipitated with isopropanol. After washing the pellet with 70% and then 100% ethanol, the RNA is resuspended in water.

b) Purification of the RNA poly A$^+$ Fraction

The RNA poly A$^+$ fraction is purified using the Dynabeads oligo (dT)$_{25}$ kit from DYNAL (reference 610.05) according to the procedure recommended by the manufacturer. The principle is based on the use of super-paramagnetic polystyrene beads on which a poly(dT)$_{25}$ oligonucleotide is attached. The RNA poly A$^+$ fraction is hybridized on the oligo(dT)$_{25}$ coupled to the beads which are trapped on a magnetic support.

2. Construction of the Complementary DNA Library a) Preparation of the complementary DNA Starting with 1 μg of the cortex (brain) RNA-poly A$^+$ obtained from step 2, the $^{32}$PdCTP-labelled single-strand complementary DNA is prepared (the complementary DNA obtained has a specific activity of 3000 dpm/ng) with the synthetic primer having the following sequence (comprising a BamHI site):

5'<GATCCGGGCC CTTTTTTTTT TTT<3(SEQ ID NO:5)

in a volume of 40 μl of buffer having the composition: 50 mM Tris HCl pH 8.3, 6 mM MgCl$_2$, 3 mM DTT, 40 mM KCl, containing 0.5 mM of each of the deoxynucleotide triphosphates, 40 μ Ci of α$^{32}$P dCTP and 40 U of RNasin (Promega). After incubation for one hour at 37° C., then 10 minutes at 50° C. and then a further 10 minutes at 37° C., with 200 units of the RNase H$^-$ reverse transcriptase enzyme (GIBCO-BRL reference 18064–014), 2.5 μl of EDTA are added.

b) Alkaline Hydrolysis of the RNA Matrix 7.5 μl of a 2N NaOH solution are added, followed by incubation for 5 minutes at 65° C.

c) Purification on a Sephacryl S400 Column

In order to remove the synthetic primer, the complementary DNA is purified on a column of 1 ml of sephacryl S400 (Pharmacia) equilibrated in TE buffer.

The first two radioactive fractions are pooled and precipitated with a ⅟₁₀ volume of 10 M ammonium acetate solution and 2.5 volumes of ethanol, this taking place after extraction with one volume of chloroform.

d) Homopolymeric Addition of dG

The complementary DNA is 3'-elongated with a dG "tail" with 30 units of the terminal transferase enzyme (Pharmacia 27073001). Incubation is carried out in 30 μl of buffer having the composition: 30 mM Tris HCl pH 7.6; 1 mM cobalt chloride, 140 mM cacodylic acid, 0.1 mM DTT, 1 mM dGTP for 15 minutes at 37° C., followed by addition of 2 μl of 0.5 M EDTA.

e) Steps b) and c) are Repeated Again f) Pairing of the Cloning Vector PT7T318R (Pharmacia, ref: 27–3512) and of the complementary DNA in the Presence of the Adapter.

Centrifugation is carried out, the pellet is dissolved in 5 μl of TE buffer, 6 μl (120 ng) of cloning vector PT7T318R, 1 1 (100 ng) of the adapter having the following sequence (comprising an ApaI site)

5'AAAAAAAAAAAAAGGGCCCG3'(SEQ ID NO:6)

and 1.3 1 of 500 mM NaCl solution are added, the reaction mixture is incubated for 5 minutes at 65° C. and is then allowed to cool to room temperature.

g) Ligation

The cloning vector and the single-strand cDNA are ligated in a volume of 200 μl with 10 units of the T4 phage DNA ligase enzyme (Pharmacia reference 270 87002) for 2 h at room temperature in a buffer having the composition: 50 mM Tris HCl pH 7.5, 10 mM $MgCl_2$, 1 mM ATP.

h) Synthesis of the Second Strand of the cDNA

The proteins are removed by extraction with phenol followed by an extraction with chloroform, after which a 1/10 volume of 10 mM ammonium acetate solution is added, followed by 2.5 volumes of ethanol. The mixture is centrifuged, the pellet is dissolved in buffer having the composition: 33 mM Tris acetate pH 7.9, 62.5 mM potassium acetate, 1 mM magnesium acetate and 1 mM dithiothreitol (DTT), the second complementary DNA strand is synthesized in a volume of 30 μl with 30 units of T4 phage DNA polymerase enzyme (Pharmacia, reference 270718) and a mixture of 1 mM of the four deoxynucleotide triphosphates dATP, dCTP, dGTP and dTTP, as well as two units of the protein from T4 phage gene 32 (Pharmacia, reference 27-0213) for one hour at 37° C. The mixture is extracted with phenol and the traces of phenol are removed by passage through a polyacrylamide P10 column (Biogel P10-200-400 mesh—reference 15011050—Biorad).

i) Transformation by Electroporation

*E.coli* MC 1061 cells are transformed with the recombinant DNA obtained above by electroporation using the Biorad Gene Pulser machine (Biorad) used at 2.5 kV under the conditions set out by the manufacturer, after which the bacteria are grown for one hour in so-called LB medium (Sambrook op cite) having the composition: 10 g/l bactotryptone; 5 g/l yeast extract; 10 g/l NaCl.

The number of independent clones is determined by plating out a 1/1000 dilution of the transformation after the first hour of incubation on a dish of LB medium supplemented with 1.5% agar (w/v) and 100 μg/ml of ampicillin, referred to hereinbelow as LB agar medium. The number of independent clones is $6 \times 10^5$.

3. Screening of the Library a) Preparation of the Membranes

The library clones are plated out on LB agar medium (Petri dishes of diameter 150 mm) coated with Biodyne A membranes (PALL reference BNNG 132). After one night at 37° C., the clones are transferred by contact onto new membranes. These membranes are treated by placing them on Whatman 3 MM paper soaked with the following solutions: 0.5 N NaOH, 1.5 M NaCl for 5 minutes and then 0.5 M Tris HCl pH 8, 1.5 M NaCl for 5 minutes. After treatment with proteinase K in the following buffer: 10 mM Tris HCl pH 8, 10 mM EDTA, 50 nm NaCl, 0.1% SDS, 100 μg/ml proteinase K for one hour at room temperature, the membranes are washed thoroughly in 2×SSC (sodium citrate NaCe), dried and then incubated in the oven under vacuum at 80° C. for 20 minutes.

b) Preparation of the Probe 100 ng of the nucleotide sequence of rNT-R2, which serves as a probe, are labelled by nick translation (Boehringer kit ref: 976776) according to the procedure recommended by the manufacturer, with 100 μCi of $\alpha^{32}P$ dCTP 3000 Ci/mmol (Amersham reference PB 10205). The radiolabelled nucleotides not incorporated are removed on a polyacrylamide P10 column (Biorad, reference 1504144). The probe obtained has a specific activity of about $5 \times 10^8$ dpm/μg.

c) Prehybridization and Hybridization

The membranes prepared in a) are prehybridized for 30 minutes at 42° C. in 6×SSC, 5×Denhardt's, 0.1% SDS, 50% formamide and then hybridized for a few hours in the same buffer supplemented with the probe prepared in b) in a proportion of $10^6$ dpm/ml.

d) Washing and Exposure of the Membranes

The membranes are washed twice at room temperature in 2×SSC/0.1% SDS buffer and then for one hour at 50° C. in 2×SSC/0.1% SDS. The hybridized clones are revealed with KODAK XOMAT films.

4) Sequencing of hNT-R2 and Sequence Analysis

The sequence is obtained using the Applied Biosystem kit (reference 401628) with the "373DNA sequencer". The primers used are the primers complementary to the upstream or downstream cloning region and oligonucleotides specific for the mNT-2 DNA.

Example 5

Construction of the Plasmid p2076

The sequence encoding the hNT-R2 receptor was amplified by polymerase chain reaction, PCR, from rNT-R2 (Chalon et al. FEBS Lett., 1996, 386, 91–94) with a "sense" primer carrying a Hind site, followed by a Kozak consensus sequence (Kozak N., J. Mol. Bol., 1987, 196, 947-950)

(5'CAACTCAAGCTTGCCGCCACCATGGAAACCAGCAGCCCGC-3') (SEQ ID NO:7)

and an "antisense" primer carrying an EcoRI site (5'CCGCGAATTCTCAGGTCCGGGTTTCTGGG-3') (SEQ ID NO:8)

The amplimer obtained was digested with Hind and EcoR restriction enzymes and inserted into the plasmid p658, an expression vector derived from p7055 (Miloux B. et al, Gene, 1994, 149, 341–344) in which the sequence encoding IL-2 has been replaced by a "polylinker" multiple cloning site. The plasmid obtained is p2076.

Example 6

Establishment of the Stable Line Expressing hNT-R2

CHO-dhfr− cells (Urlaub G. et al, Prot. Natl. Acad. Sci., 1980, 77, 4216–4220) were transformed with plasmid p2076 and the clones expressing the hNT-R2 receptor were isolated in selective medium and subjected to binding tests according to the techniques described previously (Poinot-Chazel et al, Biochemical J., 320, 145–151, 1996).

Figure 5A:
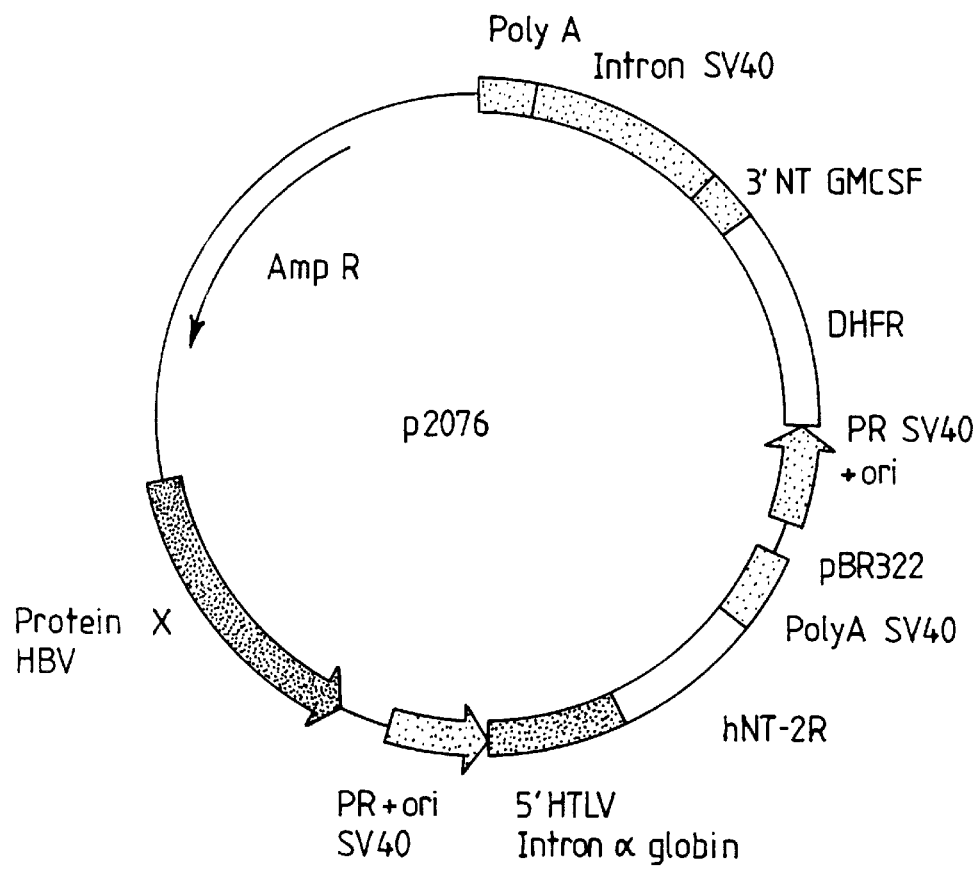
Figure 5B:
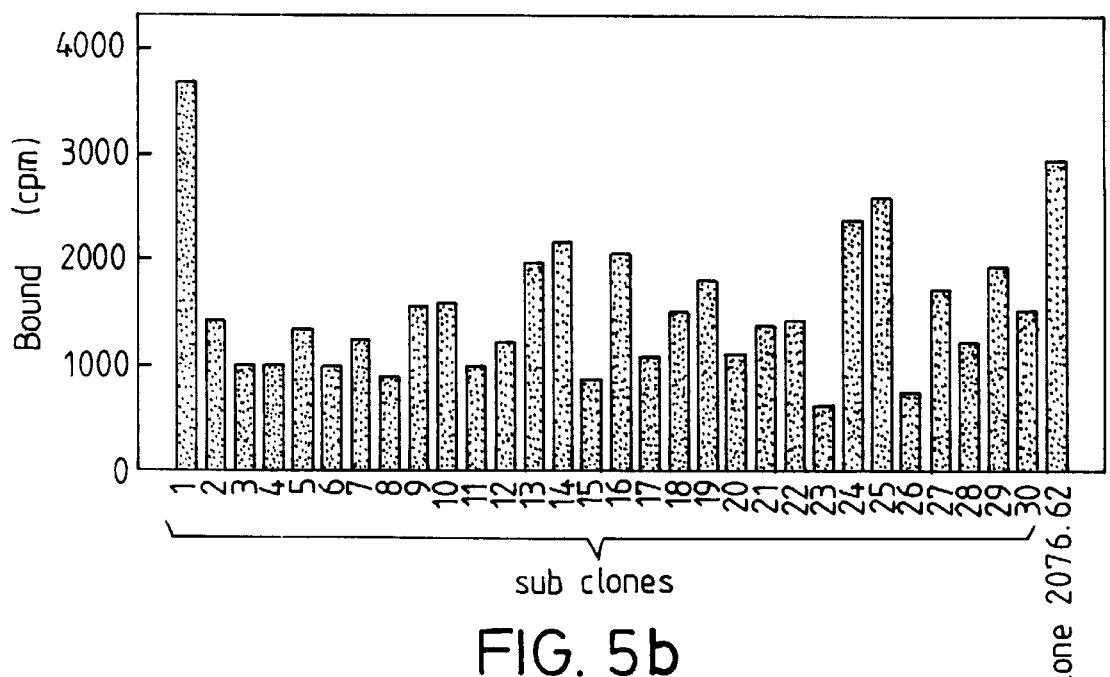
Figure 5C:
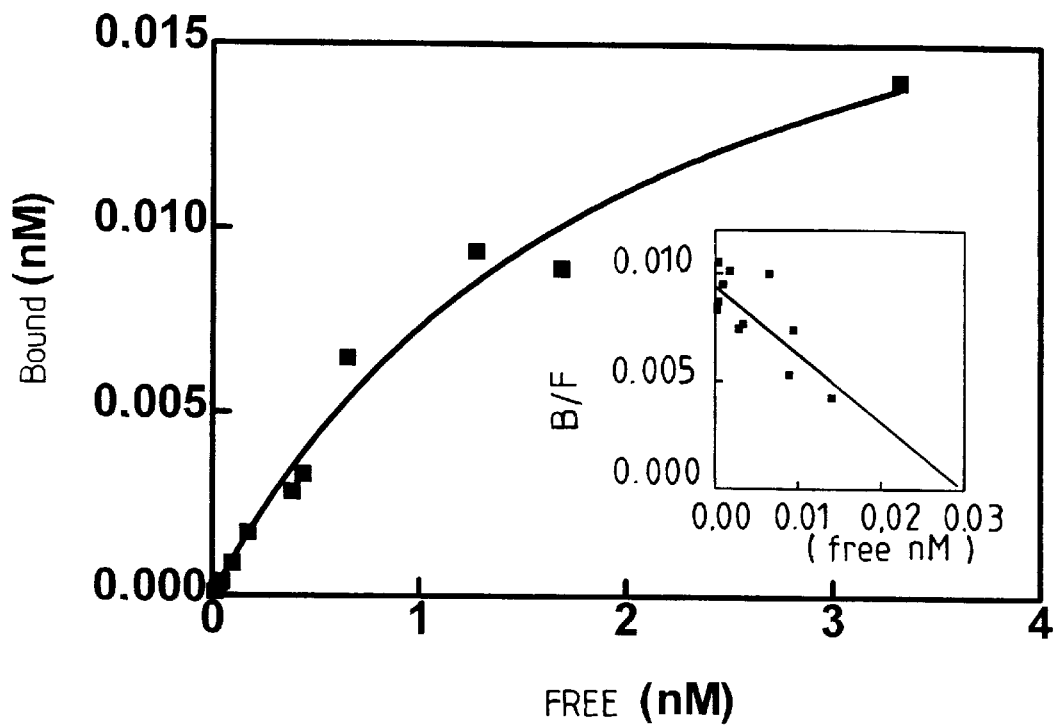
Figure 5D:
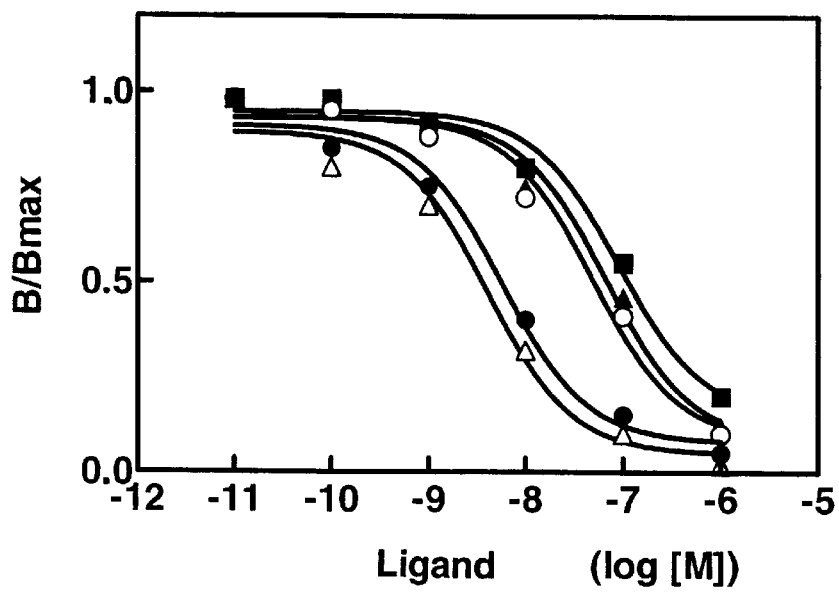

The CHO-2076-62 clone expressing the most hNT-R2 receptors was selected for the characterization studies and in order to carry out the subcloning by limiting dilution. About 30 subclones were isolated and subjected to binding tests (FIG. 5b).

The CHO–2076-2062-1 subclone showing the best level of binding was selected for the characterization studies.

Example 7

Expression of hNT-R2 mRNA.

a) Preparation of the Complementary DNA:

Total RNA is prepared as described in Example 4a. cDNA is prepared in a manner similar to that described in Example 5a, with 5 µg of total RNA, using a poly(T)12 primer. The reaction is not interrupted with EDTA.

b) Specific Amplification of Human cDNA by the Technique Known as PCR.

The polymerization is carried out with 2 µl of cDNA in 50 µl final with the following buffer: 10 nM Tris-HCl pH 8.3, 50 mM Kcl, 2.5 nM $MgCl_2$, in the presence of 10% DMSO, 0.5 mM dNTP, 2 µg/ml of each of the 2 nucleotide primers and 2.5 units of Taq polymerase (Beckman).

The primer pairs were chosen on the nucleotide sequence of hNT-R2 (clone 6.1), (SEQ ID No. 1): in position 736 for the sense primer and position 1269 for the antisense primer.

sense primer: 5'CTGGCCCTCTGCTCCCAA3' SEQ ID NO:9 antisense primer: 5'TCAGGTCCGGGTTTCTGGG3' SEQ ID NO:10

The reaction is carried out over 30 cycles, 94° C./1 minute, 58° C./1 minute, 72° C./1 minute followed by a final cycle of 72° C. for 10 minutes.

c) Expression of the hNT-R2 Messenger RNA by the Technique Known as Northern Blot.

The messenger RNAs are prepared as described in Example 4b and analysed by electrophoresis on 1% agarose gel in the presence of formaldehyde ("Molecular Cloning" T. Maniatis, E. F. Fritsch, J. Sambrook CSH), followed by transfer onto nylon membrane (hybond N+ Amersham). Expression of the messengers from different parts of human brain is analysed on a Northern blot from Clontech (ref: 7750-1). The hybridization is carried out according to the procedure described below.

The membrane is hybridized with a probe radiolabelled with dCTP $\alpha^{32}P$ (Amersham) manufactured from the cDNA of the clone 6.1 by the technique known as PCR by polymerization of the coding part of the cDNA with the nucleic acid primers in position 37 for the sense primer and in position 1286 for the antisense primer.

sense primer: 5'ATGGAAACCAGCAGCCCGC3' SEQ ID NO:11 antisense primer: 5'TCATTCTTGCATTACATTCAGG3' SEQ ID NO:12

The polymerization is carried out with 10 ng of the plasmid 6.1 under the conditions described in Example 7 paragraph b. Radiolabelling is carried out by the "random-priming" method under the conditions described by the manufacturer (Gibco-BRL ref: 8187SA).

The hybridization takes place at 42° C. for 16 hours in aqueous medium containing 50% formamide, 1M NaCl, 5× Denhardt solution and 0.1% SDS. The membrane is washed several times at room temperature with 2×SSC solution containing 0.1% SDS and then washed at 50° C. for one hour with a 0.1×SSC solution containing 0.1% SDS. The 5× Denhardt solution has the following composition: 1 g/l Ficoll (type 400-Pharmacia), 1 g/l polyvinylpyrrolidone and 1 g/l BSA. The 1×SSC solution contains 0.15M NaCl and 0.0015 M sodium citrate.

Example 8

Pharmacological Characteristics of hNT-R2

Cloning of hNTR-2 and construction of the CHO 2076.62 (hNT-R2) line allowed pharmacological characterization of this receptor. The binding experiments on this line showed results equivalent to those obtained in transient expression on COS cells or on CHC cells expressing the receptor from rats (Chalon et al. FEBS lett., 386, 91–94, 1996).

For the binding experiments, the adherent cells (CHO-2076-62) seeded in six-well plates were washed twice with 50 mM Tris-HCl, pH 7.5, 0.2% BSA, 0.1% $NaN_3$, 1 mM 1,10-ortho-phenanthroline (binding buffer). The saturation experiments were carried out in a final volume of 1.5 ml of binding buffer containing different concentrations of $[^{125}I]$-NT (from 0.05 to 10 nM). After 1 h at room temperature, the buffer is aspirated and the cells are washed twice with the same buffer. Lastly, the cells are solubilized with 2 ml of 1N NaCH and the bound radioactivity is quantified in a γ counter. The non-specific binding was defined as the binding obtained in the presence of a (500-fold) excess of non-radioactive ligand.

The competition experiments were carried out in a similar manner using a concentration of 0.2 nM $[^{125}I]$-NT as ligand. Different concentrations of non-radioactive ligands were used: neurotensin, neuromedin, levocabastine, SR48692, SR142948.

The binding results derived from the saturation and competition experiments were analysed using the GraphPad Prism 2.01 software [GraphPad Software, San Diego Calif.).

Given that levocabastine binds to this receptor, this product was tested on the hNT-R2 line. A weak but reproducible and significant signal was found using 1 mM levocabastine. Moreover, SR142948 (non-peptide hNT-R1 antagonist) was able to induce a response in the absence of levocabastine or other "agonist".

This agonist response of SR142948 was studied thoroughly in the Cytosensor. Indeed, dose-response curves were produced with this product as well as with SR48692, for which an agonist effect, although less pronounced, was found.

Moreover, the agonist effect of SR142948 may be antagonized by neurotensin or by SR48692 (at doses at which there is no agonist effect). The inhibition curves demonstrated that SR48692 is more effective than neurotensin at inhibiting the effect of SR142948.

Agonist effects of SR142948 on the CHO 2076.62 (hNT-R2) line were thus demonstrated.

The CHO-2076.62 (hNT-R2) line was used to study the signalization mechanisms involved. For example, by studying the route by which inositol phosphates are produced, a slight and transient (20-second) increase in $IP_3$ was observed in response to SR142948 but not with neurotensin.

In agreement with the microphysiometry results, the agonist effect of SR142948 and of SR48692 may be antagonized by neurotensin.

In parallel, the intracellular concentration of $Ca^{2+}$ in response to neurotensin, SR142948 and SR48692 was measured. Under these conditions, SR48692 and SR142948 show a significant response. In principle, this increase in the concentration of intracellular calcium ions is due to the release of internal reservoirs and not to the influx of extracellular calcium since the same response was found in the absence of extracellular calcium.

The fact that neurotensin does not overall exert a net agonist effect on hNT-R2 suggests that another potential natural ligand for the hNT-R2 receptor may exist. Starting with bovine brain homogenates, followed by steps of purification by different types of columns (ion exchange, gel filtration), fractions were chosen on the basis of the inhibition of the binding of [$^{125}$I]-neurotensin to hNT-R2. Using this approach, two peptides were identified. Sequencing of these peptides allowed them to be characterized and synthesized. The synthetic peptides tested in binding experiments inhibit the binding of [$^{125}$I]-neurotensin to CHO-hNT-R2 cell membranes, with an $IC_{50}$ of about 30 nM.

Example 9

Microphysiometry Studies

The microphysiometry experiments were carried out with the Cytosensor Microphysiometer (Molecular Devices, Menlo Park, Calif.). Each chamber of the instrument containing $3 \times 10^5$ cells was perfused with DMEM medium (Sigma, St. Louis, Mo.) containing 40 mM NaCl at 37° C. The rate of acidification was measured every 60 seconds (flowrate 100 ml/min). 15-second injections of agonists were carried out. For the inhibition experiments, cells were exposed to the antagonists for 30 minutes before being perfused with the agonist.

The CHO 2076.62 (hNT-R2) line was used successfully in our microphysiometry (Cytosensor) experiments. However, neurotensin triggers no signal using this technique on hNT-R2 (under the same conditions, neurotensin had a response of 200% with hNT-R1).

We claim:

1. An isolated or purified NT-R2 polypeptide comprising the amino acid sequence of SEQ ID No. 2 or SEQ ID No. 4.

2. A pharmaceutical composition for treatment of hormonal or neurological disorders in which the natural NT-R2 receptor and/or neurotensin is involved, comprising an NT-R2 polypeptide according to claim 1, combined with a pharmaceutically acceptable vehicle.

* * * * *